(12) United States Patent
Roeder et al.

(10) Patent No.: US 8,728,148 B2
(45) Date of Patent: May 20, 2014

(54) DIAMETER REDUCING TIE ARRANGEMENT FOR ENDOLUMINAL PROSTHESIS

(75) Inventors: Blayne A. Roeder, Bloomington, IN (US); Megan Bube, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 91 days.

(21) Appl. No.: 13/292,698

(22) Filed: Nov. 9, 2011

(65) Prior Publication Data

US 2013/0116773 A1    May 9, 2013

(51) Int. Cl.
*A61F 2/82* (2013.01)

(52) U.S. Cl.
USPC ........ 623/1.23; 623/1.11; 623/1.13; 623/1.35

(58) Field of Classification Search
USPC ...................................... 623/1.23
See application file for complete search history.

(56) References Cited

U.S. PATENT DOCUMENTS

| | | | |
|---|---|---|---|
| 4,902,508 A | 2/1990 | Badylak et al. | 424/95 |
| 5,035,706 A | 7/1991 | Giantureo et al. | 606/198 |
| 5,387,235 A | 2/1995 | Chuter | 623/1 |
| 5,425,765 A | 6/1995 | Tiefenbrun et al. | 623/12 |
| 5,443,500 A | 8/1995 | Sigwart | 623/1 |
| 5,445,600 A | 8/1995 | Abdulla | 604/9 |
| 5,456,713 A | 10/1995 | Chuter | 623/1 |
| 5,554,389 A | 9/1996 | Badylak et al. | 424/558 |
| 5,562,726 A | 10/1996 | Chuter | 623/1 |
| 5,609,627 A | 3/1997 | Goicoechea et al. | 623/1 |
| 5,628,783 A | 5/1997 | Quiachon et al. | 623/1 |
| 5,676,696 A | 10/1997 | Marcade | 623/1 |
| 5,676,697 A | 10/1997 | McDonald | 623/1 |
| 5,720,776 A | 2/1998 | Chuter et al. | 623/1 |
| 5,776,142 A | 7/1998 | Gunderson | 606/108 |
| 5,824,055 A | 10/1998 | Spiridigliozzi et al. | 623/1 |
| 5,843,158 A | 12/1998 | Lenker et al. | 623/1 |

(Continued)

FOREIGN PATENT DOCUMENTS

| | | | | |
|---|---|---|---|---|
| EP | 1847234 A1 | 10/2007 | | A61F 2/06 |
| EP | 2298248 A1 | 3/2011 | | |

(Continued)

OTHER PUBLICATIONS

European Search Report, dated Jan. 15, 2013, pp. 1-7, European Patent Application No. 12275169.6, European Patent Office, The Netherlands.

(Continued)

*Primary Examiner* — Thomas J Sweet
*Assistant Examiner* — Megan Wolf
(74) *Attorney, Agent, or Firm* — Brinks Gilson & Lione

(57) ABSTRACT

An endoluminal prosthesis may include a tubular body of a biocompatible graft material having proximal and distal ends and anterior and posterior sides. The prosthesis may include at least a first and a second fenestration. The first and second fenestrations may be spaced from one another circumferentially around the tubular body. The prosthesis may include at least one first diameter reducing tie positioned circumferentially on the posterior side of the prosthesis and engaging at least a circumferential segment of the posterior side to restrain the engaged segment from expansion. The prosthesis may include at least one second diameter reducing tie positioned circumferentially between the first and second fenestrations on the anterior side of the prosthesis and engaging at least a circumferential segment of the anterior side to restrain the engaged segment from expansion.

17 Claims, 9 Drawing Sheets

(56) References Cited

U.S. PATENT DOCUMENTS

| | | | | |
|---|---|---|---|---|
| 5,843,162 A | 12/1998 | Inoue | | 623/1 |
| 5,873,906 A | 2/1999 | Lau et al. | | 623/1 |
| 5,948,017 A | 9/1999 | Taheri | | 623/1 |
| 5,984,955 A | 11/1999 | Wisselink | | 623/1 |
| 5,993,844 A | 11/1999 | Abraham et al. | | 424/423 |
| 6,019,788 A | 2/2000 | Butters et al. | | 623/1 |
| 6,099,548 A | 8/2000 | Taheri | | 606/198 |
| 6,099,567 A | 8/2000 | Badylak et al. | | 623/1 |
| 6,106,549 A | 8/2000 | Taheri | | 623/1.23 |
| 6,176,875 B1 | 1/2001 | Lenker et al. | | 623/1.49 |
| 6,183,504 B1 | 2/2001 | Inoue | | 623/1.11 |
| 6,187,033 B1 | 2/2001 | Schmitt et al. | | 623/1 |
| 6,206,931 B1 | 3/2001 | Cook et al. | | 623/23.75 |
| 6,210,429 B1 | 4/2001 | Vardi et al. | | 623/1.11 |
| 6,254,629 B1 | 7/2001 | Inoue | | 623/1.13 |
| 6,287,333 B1 | 9/2001 | Appling et al. | | 623/1.22 |
| 6,350,277 B1 | 2/2002 | Kocur | | 623/1.11 |
| 6,381,350 B1 | 4/2002 | Klingensmith et al. | | 382/128 |
| 6,395,018 B1 | 5/2002 | Castaneda | | 623/1.13 |
| 6,471,722 B1 | 10/2002 | Inoue | | 623/1.35 |
| 6,485,515 B2 | 11/2002 | Strecker | | 623/6.12 |
| 6,514,286 B1 | 2/2003 | Leatherbury et al. | | 623/11.11 |
| 6,524,335 B1 | 2/2003 | Hartley et al. | | 623/1.13 |
| 6,551,350 B1 | 4/2003 | Thornton et al. | | 623/1.13 |
| 6,576,009 B2 | 6/2003 | Ryan et al. | | 623/1.35 |
| 6,592,614 B2 | 7/2003 | Lenker et al. | | 623/1.13 |
| 6,645,242 B1 | 11/2003 | Quinn | | 623/1.16 |
| 6,663,666 B1 | 12/2003 | Quiachon et al. | | 623/1.35 |
| 6,695,875 B2 | 2/2004 | Stelter et al. | | 623/1.13 |
| 6,716,238 B2 | 4/2004 | Elliott | | 623/1.11 |
| 6,723,116 B2 | 4/2004 | Taheri | | 623/1.11 |
| 6,793,672 B2 | 9/2004 | Khosravi et al. | | 623/1.13 |
| 6,805,706 B2 | 10/2004 | Solovay et al. | | 623/1.15 |
| 6,827,726 B2 | 12/2004 | Parodi | | 606/194 |
| 6,878,161 B2 | 4/2005 | Lenker | | 623/1.13 |
| 6,916,335 B2 | 7/2005 | Kanji | | 623/1.11 |
| 6,918,925 B2 | 7/2005 | Tehrani | | 623/1.11 |
| 6,929,659 B2 | 8/2005 | Pinchuk | | 623/1.13 |
| 6,939,370 B2 | 9/2005 | Hartley et al. | | 623/1.11 |
| 6,942,879 B2 | 9/2005 | Humes | | 424/529 |
| 6,974,471 B2 | 12/2005 | Van Schie et al. | | 623/1.12 |
| 7,014,653 B2 | 3/2006 | Ouriel et al. | | 623/1.14 |
| 7,022,132 B2 | 4/2006 | Kocur | | 623/1.11 |
| 7,169,176 B2 | 1/2007 | Lauterjung | | 623/1.35 |
| 7,232,459 B2 | 6/2007 | Greenberg et al. | | 623/1.13 |
| 7,238,198 B2 | 7/2007 | Hartley et al. | | 623/1.13 |
| 7,294,147 B2 | 11/2007 | Hartley | | 623/1.13 |
| 7,306,623 B2 | 12/2007 | Watson | | 623/1.16 |
| 7,407,509 B2 | 8/2008 | Greenberg et al. | | 623/1.35 |
| 7,435,253 B1 | 10/2008 | Hartley et al. | | 623/1.12 |
| 7,537,606 B2 | 5/2009 | Hartley et al. | | 623/1.11 |
| 7,645,298 B2 | 1/2010 | Hartley et al. | | 623/1.35 |
| 7,678,141 B2 | 3/2010 | Greenan et al. | | 623/1.13 |
| 7,771,462 B1 | 8/2010 | Davidson et al. | | 623/1.11 |
| 7,806,917 B2 | 10/2010 | Xiao | | 623/1.13 |
| 7,914,572 B2 | 3/2011 | Hartley et al. | | 623/1.35 |
| 2001/0012943 A1 | 8/2001 | Shaolian et al. | | 606/108 |
| 2002/0045930 A1 | 4/2002 | Burg et al. | | 623/1.11 |
| 2002/0058992 A1 | 5/2002 | Greenhalgh | | 623/1.35 |
| 2002/0177890 A1 | 11/2002 | Lenker | | 623/1.12 |
| 2002/0193872 A1 | 12/2002 | Trout, III et al. | | 623/1.34 |
| 2003/0088305 A1 | 5/2003 | Van Schie et al. | | 623/1.12 |
| 2003/0120332 A1 | 6/2003 | Hartley | | 623/1.13 |
| 2003/0149475 A1 | 8/2003 | Hyodoh et al. | | 623/1.19 |
| 2003/0199967 A1 | 10/2003 | Hartley et al. | | 623/1.13 |
| 2003/0233140 A1 | 12/2003 | Hartley et al. | | 623/1.11 |
| 2004/0054280 A1 | 3/2004 | McMorrow et al. | | 600/437 |
| 2004/0073289 A1 | 4/2004 | Hartley | | 623/1.13 |
| 2004/0093055 A1 | 5/2004 | Bartorelli et al. | | 623/1.13 |
| 2004/0098079 A1 | 5/2004 | Hartley et al. | | 623/1.11 |
| 2004/0098084 A1 | 5/2004 | Hartley et al. | | 623/1.11 |
| 2004/0106972 A1 | 6/2004 | Deaton | | 623/1.1 |
| 2004/0106978 A1 | 6/2004 | Greenberg et al. | | 623/1.13 |
| 2004/0171932 A1 | 9/2004 | Raman et al. | | 600/425 |
| 2004/0215327 A1 | 10/2004 | Doig et al. | | 623/1.16 |
| 2004/0230287 A1 | 11/2004 | Hartley et al. | | 623/1.12 |
| 2005/0049674 A1 | 3/2005 | Berra et al. | | 623/1.13 |
| 2005/0060018 A1 | 3/2005 | Dittman | | 623/1.11 |
| 2005/0102021 A1 | 5/2005 | Osborne | | 623/1.13 |
| 2005/0131517 A1 | 6/2005 | Hartley et al. | | 623/1.13 |
| 2005/0131518 A1 | 6/2005 | Hartley et al. | | 623/1.13 |
| 2005/0149166 A1 | 7/2005 | Schaeffer et al. | | 623/1.13 |
| 2005/0171597 A1 | 8/2005 | Boatman et al. | | 623/1.22 |
| 2005/0171598 A1 | 8/2005 | Schaeffer | | 623/1.35 |
| 2005/0182476 A1 | 8/2005 | Hartley et al. | | 623/1.11 |
| 2005/0222668 A1 | 10/2005 | Schaeffer et al. | | 623/1.13 |
| 2005/0222669 A1 | 10/2005 | Purdy | | 623/1.13 |
| 2005/0222672 A1 | 10/2005 | Shmulewitz | | 623/1.15 |
| 2005/0228488 A1 | 10/2005 | Nazzaro | | 623/1.26 |
| 2005/0273155 A1 | 12/2005 | Bahler et al. | | 623/1.13 |
| 2006/0004433 A1 | 1/2006 | Greenberg et al. | | 623/1.11 |
| 2006/0058864 A1 | 3/2006 | Schaeffer et al. | | 623/1.11 |
| 2006/0247760 A1 | 11/2006 | Ganesan et al. | | 623/1.16 |
| 2007/0043425 A1 | 2/2007 | Hartley et al. | | 623/1.12 |
| 2007/0142896 A1 | 6/2007 | Anderson et al. | | 623/1.13 |
| 2007/0219614 A1 | 9/2007 | Hartley | | 623/1.11 |
| 2007/0233220 A1 | 10/2007 | Greenan | | 623/1.11 |
| 2007/0250154 A1 | 10/2007 | Greenberg et al. | | 623/1.13 |
| 2007/0276468 A1 | 11/2007 | Holzer et al. | | 623/1.35 |
| 2007/0299499 A1 | 12/2007 | Hartley et al. | | 623/1.11 |
| 2008/0033354 A1 | 2/2008 | Hartley et al. | | 604/103.05 |
| 2008/0109065 A1 | 5/2008 | Bowe | | 623/1.13 |
| 2008/0114438 A1 | 5/2008 | Hartley et al. | | 623/1.11 |
| 2008/0294234 A1 | 11/2008 | Hartley et al. | | 623/1.12 |
| 2009/0125095 A1 | 5/2009 | Bui et al. | | 623/1.13 |
| 2009/0149939 A1 | 6/2009 | Godlewski et al. | | 623/1.13 |
| 2009/0171438 A1 | 7/2009 | Chuter et al. | | 623/1.13 |
| 2009/0171451 A1 | 7/2009 | Kuppurathanam et al. | | 623/1.36 |
| 2009/0171454 A1 | 7/2009 | Parker | | 623/1.46 |
| 2009/0204202 A1 | 8/2009 | Dierking et al. | | 623/1.16 |
| 2009/0240316 A1 | 9/2009 | Bruszewski | | 623/1.13 |
| 2009/0254170 A1 | 10/2009 | Hartley et al. | | 623/1.12 |
| 2009/0259290 A1 | 10/2009 | Bruszewski et al. | | 623/1.13 |
| 2009/0264821 A1 | 10/2009 | Mafi et al. | | 604/103.01 |
| 2010/0023110 A1 | 1/2010 | Schaeffer | | 623/1.13 |
| 2010/0063576 A1 | 3/2010 | Schaeffer et al. | | 623/1.13 |
| 2010/0161027 A1 | 6/2010 | Orr | | 623/1.13 |
| 2010/0198328 A1 | 8/2010 | Hartley et al. | | 623/1.11 |
| 2010/0249899 A1 | 9/2010 | Chuter et al. | | 623/1.13 |
| 2010/0268327 A1 | 10/2010 | Bruszewski et al. | | 623/1.18 |
| 2011/0054594 A1 | 3/2011 | Mayberry et al. | | 623/1.34 |
| 2011/0166640 A1 | 7/2011 | Leewood et al. | | 623/1.15 |
| 2011/0264192 A1 | 10/2011 | Hartley et al. | | |

FOREIGN PATENT DOCUMENTS

| | | | | |
|---|---|---|---|---|
| JP | 2005-000569 | | 1/2005 | A61M 29/02 |
| JP | 2005-058459 | | 3/2005 | A61M 29/02 |
| WO | WO 03/101518 A1 | | 12/2003 | |
| WO | WO 2004/002365 A1 | | 1/2004 | A61M 25/00 |
| WO | WO 2004/002370 A1 | | 1/2004 | A61F 20/00 |
| WO | WO 2004/017867 A1 | | 3/2004 | A61F 2/06 |
| WO | WO 2004/017868 A1 | | 3/2004 | A61F 2/06 |
| WO | WO 2004/028399 A2 | | 4/2004 | |
| WO | WO 2005/034808 A1 | | 4/2005 | A61F 2/06 |
| WO | WO 2005/034810 A1 | | 4/2005 | A61F 2/06 |

OTHER PUBLICATIONS

U.S. Appl. No. 13/213,349, filed Aug. 19, 2011.
U.S. Appl. No. 61/375,815, filed Aug. 21, 2010.
Branched and Fenestrated Stent-Grafts presentation, Tim Chuter, MD, 15 pages.
Branched Stent-Grafts presentation, Tim Chuter, MD, 24 pages.
Branched Stent-Grafts presentation, Tim Chuter, MD, 2002, 30 pages.
Branched Stent-Grafts presentation, Tim Chuter, MD, 29 pages.
Endovascular AAA Repair presentation, Tim Chuter, MD, 2002, 56 pages.
Endovascular AAA Repair presentation, Tim Chuter, MD, 2002, 44 pages.
Endovascular AAA Repair presentation, Tim Chuter, MD, Division of Vascular Surgery, University of California San Francisco, updated Sep. 2002, Part 1—50 pages and Part 2—44 pages.

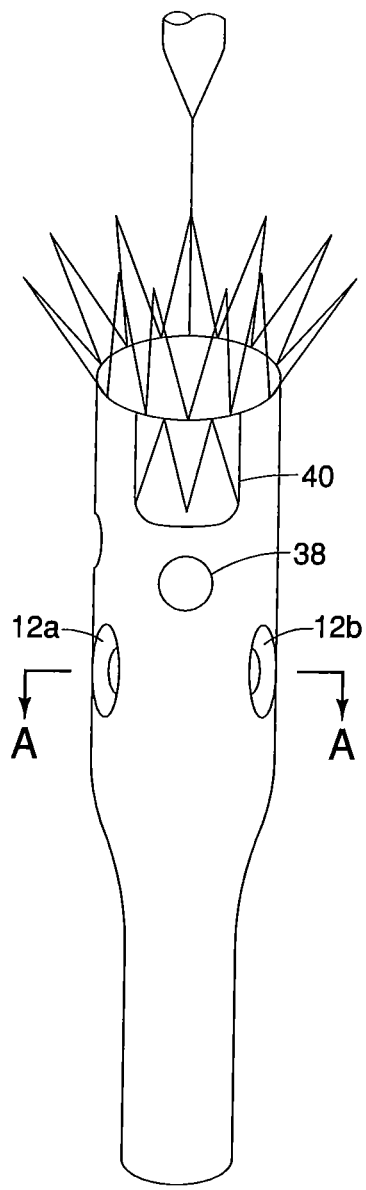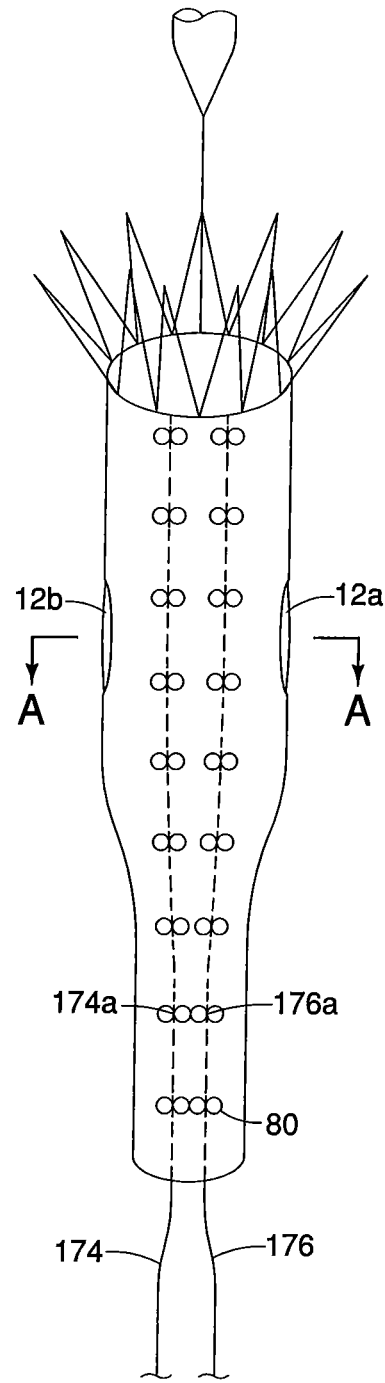
FIG. 11
FIG. 12

DIAMETER REDUCING TIE ARRANGEMENT FOR ENDOLUMINAL PROSTHESIS

TECHNICAL FIELD

This disclosure relates generally to medical devices and, more particularly, to endoluminal medical devices for implantation within the human or animal body for treatment of endovascular disease.

BACKGROUND

Using stent grafts to treat aneurysms is common in the medical field. Stent grafts are deployed by accessing a vasculature with a small incision in the skin and guiding a delivery system to the target area. This intraluminal delivery is less invasive and generally preferred over more intrusive forms of surgery. Multiple stent grafts may be implanted using intraluminal delivery to provide a system of interconnected stent grafts. Interconnected stent grafts can include fenestrated stent grafts and smaller side branch grafts, including bifurcated components.

Sometimes aneurysms engulf a vessel and its branch vessels, such as the aorta and the renal arteries or the aortic arch and the branch arteries. In such instances, a fenestrated graft can be implanted in the main vessel while smaller branch grafts can be deployed in the branch arteries. The main vessel graft may have fenestrations that correspond with the openings of the branch vessels. The smaller branch grafts are joined with the main vessel graft at the fenestrations. This juncture can be subject to significant stress caused by movement of the endovascular system.

Moreover, when a condition such as an aneurysm has engulfed a main vessel and multiple branch vessels, it may be difficult and relatively time consuming to align the fenestrations of the main graft with the branch vessels to deliver the smaller branch grafts needed in addition to the main graft. For example, when multiple smaller branch grafts must be deployed to cannulate multiple corresponding branch vessels, insertion of the required wire guides and delivery devices may be difficult and time consuming.

SUMMARY

The present embodiments provide an endoluminal prosthesis and systems and methods for facilitating deployment of such a prosthesis.

In one example, an endoluminal prosthesis may include a tubular body of a biocompatible graft material. The tubular body may have a proximal end, a distal end, an anterior side, and a posterior side. The prosthesis may include at least a first fenestration and a second fenestration in the graft material of the tubular body. The first and second fenestrations may be spaced from one another circumferentially around the tubular body of the prosthesis. The prosthesis may include at least one first diameter reducing tie. The first diameter reducing tie may be positioned circumferentially on the posterior side of the prosthesis. The first diameter reducing tie may engage at least a circumferential segment of the posterior side of the tubular body of the prosthesis. The engaged segment of the posterior side of the tubular body may be restrained from expansion by the first diameter reducing tie. The prosthesis may include at least one second diameter reducing tie. The second diameter reducing tie may be positioned circumferentially between the first and second fenestrations on the anterior side of the prosthesis. The second diameter reducing tie may engage at least a circumferential segment of the anterior side of the tubular body of the prosthesis. The engaged segment of the anterior side of the tubular body may be restrained from expansion by the second diameter reducing tie.

In another example, an endoluminal prosthesis may include a tubular body of a biocompatible graft material. The tubular body may have a proximal end, a distal end, and at least one stent positioned on the graft material. A first series of diameter reducing ties may be positioned circumferentially on a posterior side of the prosthesis. The first series of diameter reducing ties may be arranged in a substantially linear arrangement extending generally longitudinally between the proximal and distal ends of the prosthesis. Each diameter reducing tie of the first series of diameter reducing ties may be engaged by a first release wire. Each diameter reducing tie of the first series of diameter reducing ties may engage a circumferential segment of the posterior side of the prosthesis to restrain the engaged segment from expansion. A second series of diameter reducing ties may be positioned circumferentially on an anterior side of the prosthesis. The second series of diameter reducing ties may be engaged by a second release wire. Each diameter reducing tie of the second series of diameter reducing ties may engage a circumferential segment of the anterior side of the prosthesis to restrain the engaged segment from expansion.

In another example, a method of restraining at least a portion of an endoluminal prosthesis from expansion may include positioning a first release wire on a posterior side of the prosthesis in a reduced diameter configuration. The method also may include positioning a second release wire on an anterior side of the prosthesis in the reduced diameter configuration and circumferentially between a first fenestration and a second fenestration of the prosthesis. The first and second fenestrations may be spaced from one another along a circumference of the prosthesis. The method may include attaching a first series of threads to the first release wire and a corresponding series of stents of the prosthesis to form a first series of diameter reducing ties. Each stent of the series of stents may be restrained from expansion along a posterior portion of the stent. The method may include attaching a second series of threads to the second release wire and the series of stents of the prosthesis to form a second series of diameter reducing ties. Each stent of the series of stents may be restrained from expansion along an anterior portion of the stent. At least a portion of the prosthesis may be expandable from the reduced diameter configuration to an expanded configuration. An angular position of the first fenestration in the expanded configuration may be substantially the same as the angular position of the first fenestration in the reduced diameter configuration. An angular position of the second fenestration in the expanded configuration may be substantially the same as the angular position of the second fenestration in the reduced diameter configuration.

Other systems, methods, features, and advantages of the invention will be, or will become, apparent to one with skill in the art upon examination of the following figures and detailed description. It is intended that all such additional systems, methods, features, and advantages be within the scope of the invention, and be encompassed by the following claims.

BRIEF DESCRIPTIONS OF THE DRAWINGS

FIG. 11 is a perspective view of an anterior side of the prosthesis of FIG. 1 having diameter reducing ties applied thereto in one exemplary configuration.

FIG. 12 is a perspective view of a posterior side of the prosthesis of FIG. 11.

DETAILED DESCRIPTION OF THE DRAWINGS AND THE PRESENTLY PREFERRED EMBODIMENTS

Figure 1:
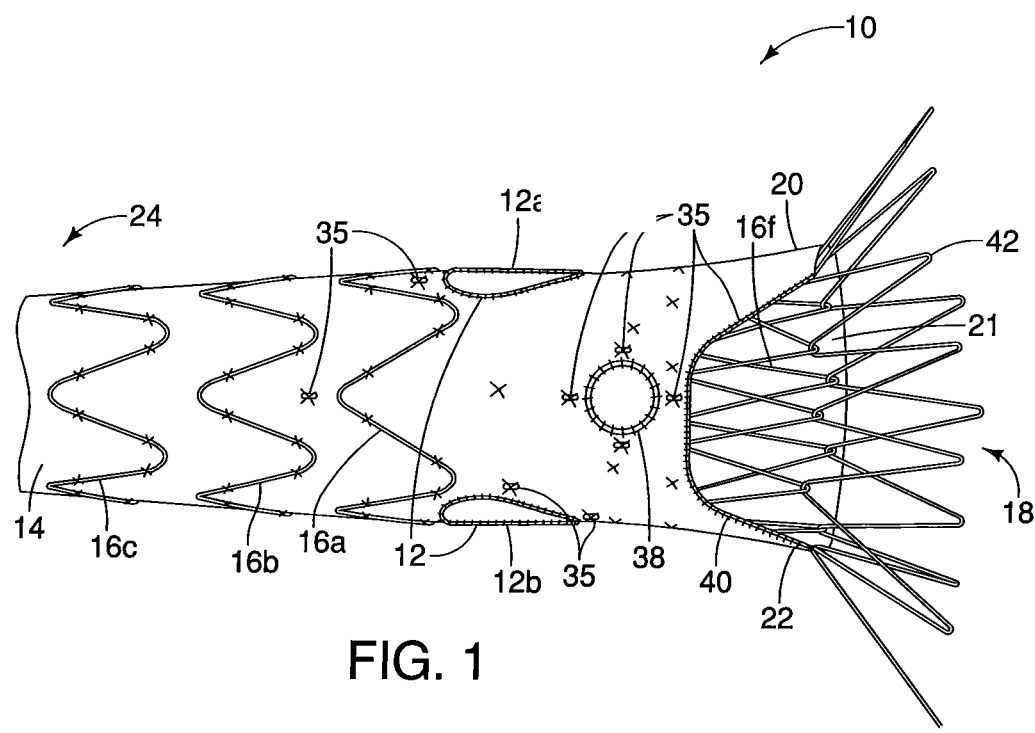
FIG. 1 is a partial perspective view of one example of a prosthesis.

The present disclosure relates to an endoluminal prosthesis and systems and methods for facilitating deployment of such a prosthesis.

In the present disclosure, the term "proximal" refers to a direction that is generally closest to the heart during a medical procedure, while the term "distal" refers to a direction that is farthest from the heart during a medical procedure.

The term "fenestration" refers to an opening provided through a surface of a prosthesis from the interior of the prosthesis to the exterior of the prosthesis. A fenestration may have any one of a variety of geometries including circular, semi-circular, oval, oblong, or other geometries.

The term "prosthesis" refers to any device for insertion or implantation into or replacement for a body part or a function of that body part. The term also may refer to a device that enhances or adds functionality to a physiological system. The term prosthesis may include, for example and without limitation, a stent, stent-graft, filter, valve, balloon, embolization coil, and the like.

FIGS. 1-4 show one example of a prosthesis 10 to which the invention may be applied. The prosthesis 10 may be configured as a stent graft and may include graft material 14. The graft material 14 may form a generally tubular body of the prosthesis 10. The prosthesis 10 may have a proximal end 22, a distal end 24, and a lumen 18 extending through the prosthesis to permit passage of blood from the proximal end 22 to the distal end 24. An anterior side of the tubular body of the prosthesis may extend circumferentially around approximately half of the circumference of the prosthesis. A posterior side of the prosthesis 10 may extend circumferentially around approximately the other half of the circumference of the prosthesis. The posterior side of the prosthesis 10 may be positioned opposite the anterior side with respect to the circumference of the prosthesis. In other words, a plane may be defined to include the longitudinal axis of the prosthesis 10. The anterior side of the prosthesis 10 may be positioned on one side of the plane, and the posterior side of the prosthesis may be positioned on the opposite side of the plane from the anterior side. The anterior side and the posterior side may cooperatively form the tubular body of the prosthesis 10.

Figure 2:
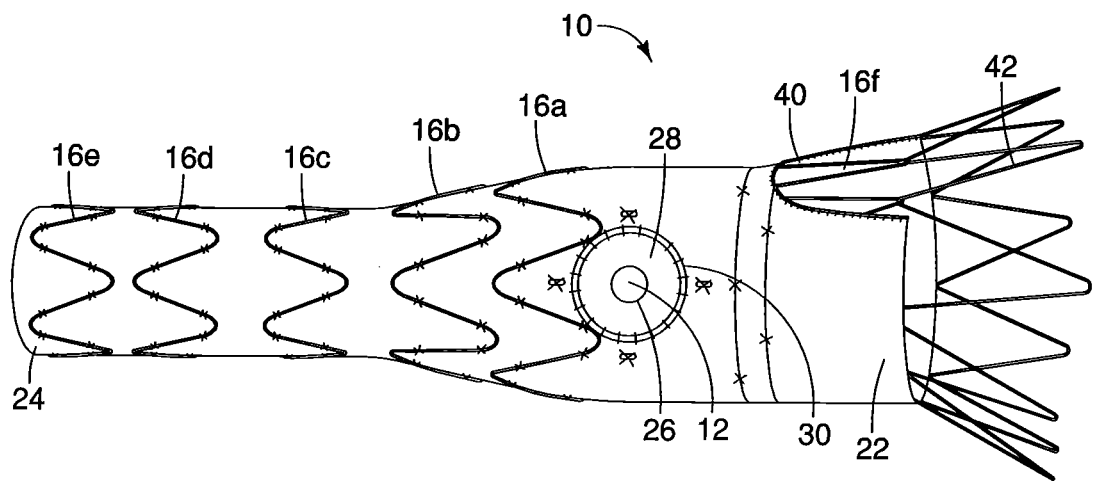
FIG. 2 is a perspective view of the prosthesis of FIG. 1 showing a pivotable fenestration.

The prosthesis 10 also may include one or more stents 16. The stents 16 may be positioned on an external surface 20 and/or an internal surface 21 of the graft material 14. In one particular embodiment, the prosthesis 10 has external body stents 16a, 16b, 16c, 16d, 16e and at least one internal stent 16f as shown in FIG. 2. The internal stent 16f may be a sealing stent placed at or near the proximal end 22 of the prosthesis 10 to seal the prosthesis to a wall of a body vessel into which the prosthesis may be placed. Additionally, or alternatively, a sealing stent may be placed at the distal end 24 of the prosthesis 10. The prosthesis 10 also may include an attachment mechanism such as an attachment stent 42 at either or both ends of the prosthesis. The attachment mechanism may further secure the prosthesis 10 within the body vessel to prevent migration of the prosthesis within the body vessel.

Figure 4:
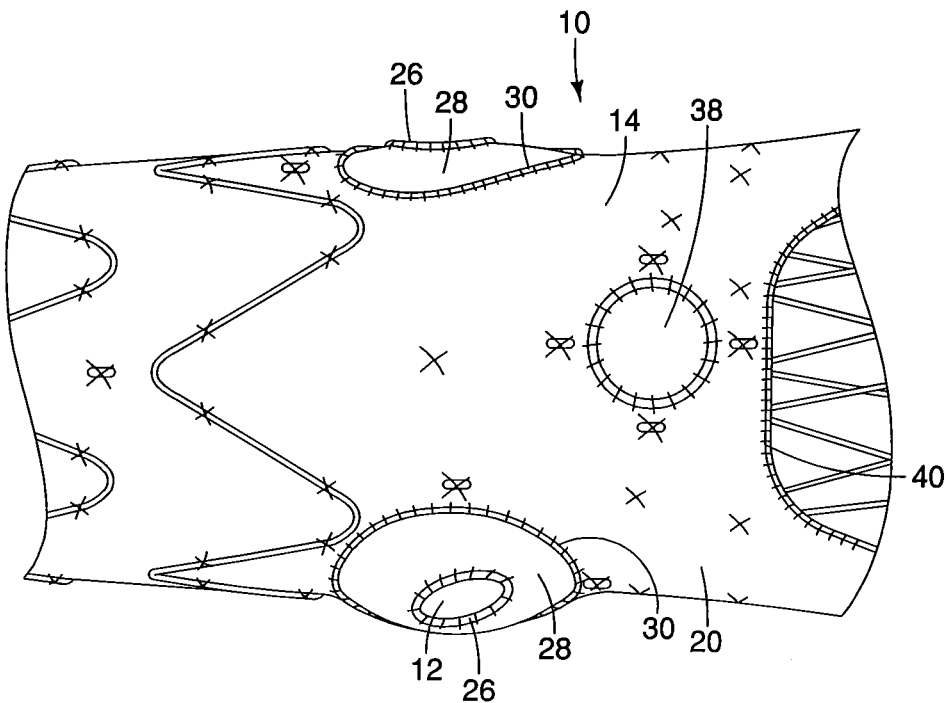
FIG. 4 is an enlarged partial perspective view of the prosthesis of FIG. 1 having pivotable fenestrations in a convex orientation.

The prosthesis 10 also may include various openings or fenestrations extending from the internal surface 21 to the external surface 20 of the graft material 14. Any of the fenestrations described herein may be pivotable or non-pivotable. For example, the prosthesis 10 may include two pivotable fenestrations 12, a fenestration 38, which may be non-pivotable, and a scallop 40 as shown in FIGS. 1-2 and 4. Although the prosthesis 10 is generally described as including two pivotable fenestrations 12 and a non-pivotable fenestration 38, the disclosure is not so limited. In other examples, any of the fenestrations may be pivotable or non-pivotable, and such examples are within the scope of this disclosure. The pivotable fenestrations 12 may be positioned on the prosthesis 10 to align with, for example, the renal arteries. It will be recognized by one of ordinary skill in the art that the prosthesis may include any number of openings or fenestrations of any type. Also, the openings or fenestrations may be arranged on the prosthesis in any manner. Preferably, the openings or fenestrations may be arranged to correspond to a particular position within the anatomy into which the prosthesis is intended to be placed.

The prosthesis 10 illustrated in FIG. 1 may be configured for placement in an abdominal aorta of a patient. The prosthesis 10 also may be configured to extend between a point proximal to the renal arteries and a point distal to the renal arteries. To that end, the scallop 40 may be configured to align with the celiac artery, the fenestration 38 may be configured to align with the superior mesenteric artery, and the pivotable fenestrations 12 may be configured to align with the renal arteries. The scallop 40 may be positioned circumferentially on an anterior point of the prosthesis 10 and longitudinally at the proximal end 22 of the prosthesis. The anterior point of the prosthesis 10 may extend generally longitudinally along the body of the prosthesis and may be substantially circumferentially centered on the anterior side of the prosthesis. The fenestration 38 may be positioned circumferentially on the anterior point of the prosthesis 10 and longitudinally distal to the scallop 40. The pivotable fenestrations 12 may be spaced from one another by a predetermined distance around the circumference of the prosthesis 10. For example the first pivotable fenestration 12a may be configured to align with the right renal artery and may be spaced a first circumferential distance from the anterior point of the prosthesis 10. The second pivotable fenestration 12b may be configured to align with the left renal artery and may be spaced a second circumferential distance from the anterior point of the prosthesis 10. The first and second circumferential distances may be of substantially equal lengths in opposite directions relative to the anterior point of the prosthesis 10. Alternatively, the first and second circumferential distances may be different from one another, for example, to correspond to the anatomy of a particular patient. The first and second pivotable fenestrations 12a, 12b may be positioned at substantially the same longitudinal position along the body of the prosthesis 10. Alternatively, the first and second pivotable fenestrations 12a, 12b may be offset longitudinally with respect to one another, for example, to correspond to the anatomy of a particular patient. The first and second pivotable fenestrations 12a, 12b may be positioned longitudinally distal to the fenestration 38 and the scallop 40.

Figure 3:
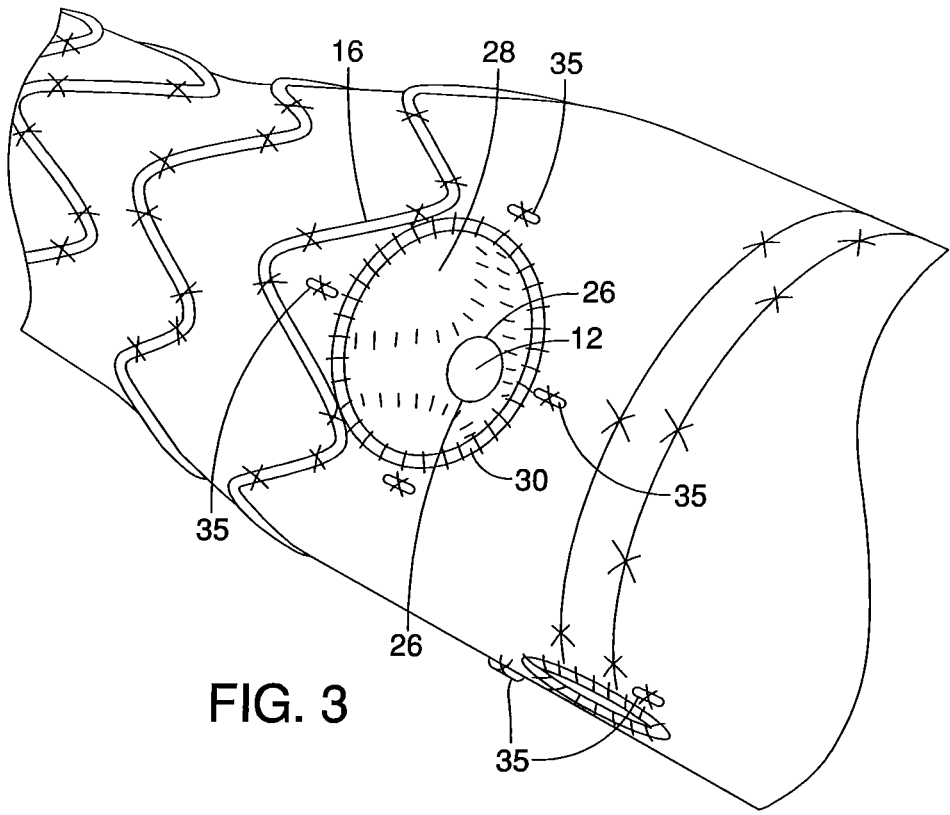
FIG. 3 is an enlarged partial perspective view of the prosthesis of FIG. 1 having a pivotable fenestration in a concave orientation.

FIG. 3 shows a close-up view of a pivotable fenestration 12. The pivotable fenestration 12 may include an inner perimeter 26 surrounding the fenestration 12, a band 28 surrounding the inner perimeter 26, and an outer perimeter 30 surrounding the band 28. The outer perimeter 30 may have a diameter that is greater than a diameter of the inner perimeter 26. The inner perimeter 26, the band 28, and the outer perimeter 30 may be substantially concentric with one another if brought into the same plane, for example, the surface plane of the graft. The inner perimeter 26, the band 28, and the outer perimeter 30 may form an extension having a hemispherical shape, resembling a dome, or a frustoconical cone extending from the surface of the graft material 14. The fenestration 12 may be positioned at the peak or top of the extension. The fenestration may be placed in a concave orientation or a convex orientation. In the concave orientation, the extension may extend into the lumen 18 of the prosthesis 10 as shown in FIGS. 1-3. In the convex orientation, the extension may extend away from the lumen as shown in FIG. 4. The pivotable fenestration may be movable between the concave orientation and the convex orientation. The pivotable fenestration also may be placed in any position between the concave orientation and the convex orientation. For example, the band 28 may be folded, bent, gathered, pleated, or otherwise manipulated such that the fenestration 12 is generally aligned with the surface plane of the prosthesis 10.

The outer perimeter 30 may be affixed to the graft material 14 by any attachment method including suturing circumferentially about an aperture disposed through the graft material 14. The band 28 may be sufficiently flexible to permit the fenestration 12 to move such that a branch prosthesis disposed in the fenestration may be oriented upwardly, downwardly, laterally, diagonally, and the like relative to the surface of the graft. In some examples, the band 28 may permit the fenestration 12 to move up to about 180 degrees relative to the surface plane of the prosthesis 10. Accordingly, the pivotable fenestration 12 may allow the prosthesis 10 to be used in a variety of patients due to its ability to adapt to the variance in the positioning of the diseased branch vessels. For example, if a branch vessel is or becomes offset longitudinally or axially from a pivotable fenestration 12, the pivotable fenestration may pivot the branch prosthesis in the necessary direction and to the necessary degree to maintain the branch prosthesis in place in the branch vessel.

As shown throughout FIGS. 1-4, imagable markers 35 may be placed at various positions on the prosthesis 10 to identify certain aspects of the prosthesis and locations of those aspects during implantation of the prosthesis within the vasculature of a patient. The markers 35 may be viewed during and after placement of the prosthesis 10 to facilitate correct placement of the fenestrations 12, 38, the scallop 40, the ends 22, 24 of the prosthesis, and the like. For example, as shown in FIG. 3, markers 35 may be placed about the circumference of the outer perimeter 30 of the pivotable fenestration 12. The markers 35 may be, for example, sewn or sutured to the graft material 14 or woven into the graft material. The markers 35 also may be placed on the struts of one or more stents 16. For example, radiopaque marker tubes may be placed about one or more struts of any of the stents. The markers 35 may be formed from any material that may be imaged by way of fluoroscopy, 3D imaging, MRI, or the like. For example, one suitable material may be gold.

The prosthesis 10 may be sized and shaped for placement within the vasculature of a patient as further described below. The preferred size and shape of the prosthesis 10 may depend on the anatomy in which it is to be implanted. Physiological variables, deployment characteristics, and other factors also may contribute to the determination of a proper size and shape of the prosthesis 10. For example, the prosthesis 10 may have a size and shape suitable for placement in the abdominal aorta. To that end, the graft body 14 of the prosthesis 10 may have a diameter, for example, ranging from about 10 mm to about 38 mm, typically from about 19 mm to about 31 mm. The diameter of the graft body 14 may be generally constant along the length thereof. Alternatively, the graft body 14 may be tapered such that the diameter of the graft body may generally increase or decrease along the length thereof. The fenestrations 12 may be configured to align with the renal arteries. Accordingly, the fenestrations 12 may have a diameter, for example, ranging from about 6 mm to about 24 mm, typically from about 6 mm to about 8 mm. The prosthesis 10 may be deployed in combination with various other prostheses to effectively bridge an aneurysmal portion of the vasculature.

The graft 14 and/or the bands 28 may be made of any material known in the art. The graft may be made of the same or a different material as the bands. Preferably, the graft and the bands may be formed from a biocompatible material that is substantially non-toxic in the in vivo environment of its intended use and substantially unrejected by the patient's physiological system (i.e., is non-antigenic). For example, the graft and/or the bands may be made of an expanded polytetrafluoroethylene (ePTFE), polytetrafluoroethylene, silicone, polyurethane, polyamide (nylon), polyethylene, polypropylene, polyaramids, polyacrylonitrile, cellulose, or another flexible biocompatible material. The graft body and/or the bands also may be made of known fabric graft materials, e.g., woven polyester such as DACRON® from Invista (Wichita, Kans.), polyetherurethanes such as THORALON® from Thoratec Corporation (Pleasanton, Calif.), or polyethylene such as an ultra-high molecular weight polyethylene (UHMwPE) such as DYNEEMA® from DSM Dyneema LLC (Stanley, N.C.). In addition, materials that are not inherently biocompatible may be subjected to surface modifications to render the materials biocompatible. Examples of surface modifications include, for example, graft polymerization of biocompatible polymers on the surface, coating of the surface with a crosslinked biocompatible polymer, chemical modification with biocompatible functional groups, or immobilization of a compatibilizing agent such as heparin or other biocompatible substances. Thus, any fibrous material having sufficient strength to survive in the in vivo environment may be used to form a textile graft, provided the final textile is biocompatible.

The graft material and/or bands also may include a bioremodelable material such as reconstituted or naturally-derived collagenous materials. Suitable remodelable materials can be provided by collagenous extracellular matrix (ECM) materials possessing biotropic properties. For example, suitable collagenous materials may include ECM materials such as those comprising submucosa, renal capsule membrane, dermal collagen, dura mater, pericardium, fascia lata, serosa, peritoneum or basement membrane layers, including liver basement membrane. Suitable submucosa materials for these purposes may include, for instance, intestinal submucosa including small intestinal submucosa, stomach submucosa, urinary bladder submucosa, and uterine submucosa. Collagenous matrices including submucosa (potentially along with other associated tissues) useful in the present invention can be obtained by harvesting such tissue sources and delaminating the submucosa-containing matrix from smooth muscle layers, mucosal layers, and/or other layers occurring in the tissue source. For additional information as to some of the materials useful in the present invention, and their isolation and treatment, reference can be made, for example, to U.S. Pat. Nos. 4,902,508, 5,554,389, 5,993,844, 6,206,931, and 6,099,567. Non-limiting example of suitable remodelable materials may include SURGISIS® BIODESIGN™ from Cook Medical (Bloomington, Ind.) or the graft prosthesis material described in U.S. Pat. No. 6,206,931 to Cook et al., which is incorporated herein by reference in its entirety. The graft bodies also may be made of any of the materials described in U.S. Pat. No. 7,407,509 to Greenberg et al. or U.S. Patent Application Pub. No. 2009/0171451 to Kuppurathanam et al., which are incorporated herein by reference in their entirety.

The stents 16 may have any suitable stent pattern known in the art. The stents may be balloon expandable. Preferably, the stents may be self-expandable. The stents can maintain the patency of the prosthesis and ensure adequate sealing against the surrounding vascular tissue. One goal for stent design and placement, whether internal or external, may be to prevent metal-to-metal contact points, prevent contact between two different types of alloys, and minimize micromotion. Stent sizing, spacing, and design may be determined so that there is no stent-to-stent contact even in tortuous anatomy. Stents preferably may be placed to maximize prosthesis flexibility while maintaining patency, as well as reduce material wear and stent fatigue. Furthermore, it is preferable that the stents do not interfere with the branch, that they minimize the potential for galvanic corrosion, and ensure adequate joint stability. Stent amplitude, spacing, and stagger preferably may be optimized for each prosthesis design. Any of the stents mentioned herein may have barbs and/or other anchoring members to help decrease prosthesis migration.

One example of a stent pattern is the Z-stent or Gianturco stent design. Each Z-stent may include a series of substantially straight segments or struts interconnected by a series of bent segments or bends. The bent segments may include acute bends or apices. The Z-stents are arranged in a zigzag configuration in which the straight segments are set at angles relative to one another and are connected by the bent segments. This design provides both significant radial force as well as longitudinal support. In tortuous anatomy, branches, or fenestrations, it may be preferable to use alternative stents or modifications to the Z-stent design to avoid stent-to-stent contact. Alternative stents may include, for example, annular or helical stents. Furthermore, in complex anatomical situations, external stents may have the potential to become intertwined with the wires or other devices utilized to ensure branch vessel access, sealing, and fixation. Thus, in some instances, it may be desirable to affix some of the stents to the internal surface of the prosthesis.

The stents described herein may be made from any suitable material known in the art. In one example, the stents may be made from standard medical grade stainless steel and are soldered using silver standard solder (0 lead/0 tin). In other examples, the stents may be made from a metallic material selected from any type of stainless steel, silver, platinum, palladium, gold, titanium, tantalum, iridium, tungsten, cobalt, chromium, cobalt-chromium alloy 1058, cobalt-based 35N alloy, nickel-based alloy 625, a molybdenum alloy, a molybdenum alloy including about 0.4% to about 0.8% of lanthanum oxide ($Li_2O_3$), and a nickel-titanium alloy, or other suitable materials known in the art. The stents also may be made from nitinol or other shape-memory metal. Moreover, the stents may be configured in a variety of ways to provide a suitable intraluminal support structure. For example, one or more stents may be made from a woven wire structure, a laser-cut cannula, individual interconnected rings, or another pattern or design.

The prosthesis 10 may include any other features including, for example, any of those described in U.S. patent application Ser. No. 13/213,349, filed Aug. 19, 2011 or U.S. Provisional Patent Application No. 61/375,815, filed Aug. 21, 2010, which are incorporated by reference herein in their entirety.

The prosthesis 10 may be compressed into a delivery configuration for delivery to a desired position within a body vessel. For example, the prosthesis 10 may be compressed into the delivery configuration, loaded onto a delivery device such as an introducer or a catheter, and covered by a sheath. The sheath may retain the prosthesis 10 in the delivery configuration. Upon retraction of the sheath, the prosthesis 10 may be allowed to expand toward an expanded configuration. It may be desirable to prevent the prosthesis 10, or at least a portion thereof, from expanding to the expanded configuration upon retraction of the sheath. Instead, at least a portion of the prosthesis 10 may be retained in a reduced diameter configuration. The diameter of the prosthesis 10, or a portion thereof, in the reduced diameter configuration may be greater than the diameter of the prosthesis in the delivery configuration, but less than the diameter of the prosthesis in the expanded configuration. One or more diameter reducing ties may be applied to the prosthesis 10 to retain the prosthesis in the reduced diameter configuration. FIGS. 5-10 illustrate examples of diameter reducing ties. For clarity, these figures depict only a portion of a stent 16 of the prosthesis 10. The remainder of the stent 16 and the graft material 14 are omitted. Suitable diameter reducing ties may include those described in U.S. Patent Application Pub. Nos. 2004/0098084 to Hartley et al., 2006/0004433 to Greenberg et al., 2007/0043425 to Hartley et al., 2007/0142896 to Anderson et al., 2008/0114438 to Hartley et al., or 2008/0294234 to Hartley et al.

Figure 5:
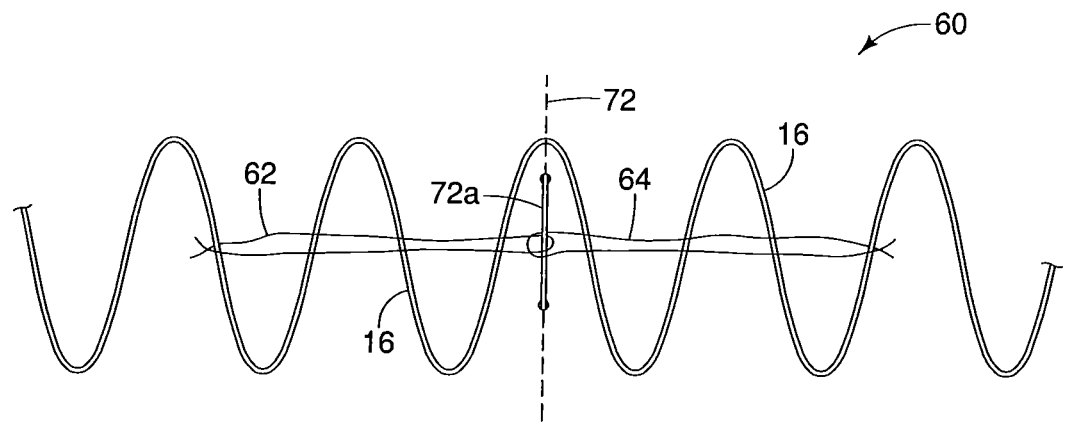
FIG. 5 depicts the formation of one example of a diameter reducing tie.
Figure 6:
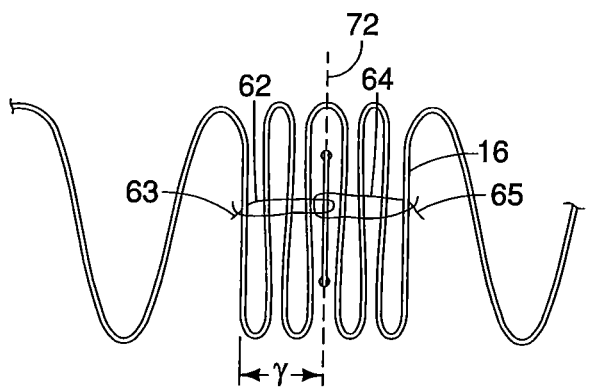
FIG. 6 depicts the diameter reducing tie formed as shown in FIG. 5.

FIGS. 5-6 depict the application of one example of a diameter reducing tie 60 to the stent 16. The stent 16 may be an internal or an external stent and may be attached to and extend circumferentially along the tubular body of the prosthesis 10 as described above. A release wire 72 may be stitched longitudinally along the graft material 14 of the prosthesis 10, with a stitch 72a being positioned outside of the prosthesis (e.g., along the external surface 20 of the graft material 14) in the region of the stent 16. A first thread 62 may be looped around the release wire 72 such that an intermediate portion of the first thread at least partially encircles the release wire and opposing end portions of the first thread extend in a first direction transverse to the release wire as shown in FIG. 5. Each of the end portions of the first thread 62 may pass over one or more struts of the stent 16. One of the end portions then may pass over a target strut and the other end portion may pass under the target strut. One of the end portions may overlap the other end portion such that the first thread 62 at least partially encircles the target strut. For example, the first thread 62 may pass over three struts and loop around a fourth strut (i.e., a target strut) as shown in FIG. 5. The two end portions of the first thread 62 may be tied in a knot 63 which may be pulled tight as shown in FIG. 6 to form one half of the diameter reducing tie 60. This may cause the struts between the release wire 72 and the knot 63 to be pulled closer to one another. Excess portions of the first thread 62 extending beyond the knot 64 may be trimmed as shown in FIG. 6.

A second thread 64 may be applied in a similar manner to another portion of the stent 16. An intermediate portion of the second thread 64 may at least partially encircle the release wire 72 or the first thread 62. Opposing end portions of the second thread 64 may extend in a second direction transverse to the release wire and generally opposite the first direction of the first thread 62 as shown in FIG. 5. Each of the end portions of the second thread 64 may pass over one or more struts of the stent 16. One of the end portions then may pass over a target strut and the other end portion may pass under the target strut. One of the end portions may overlap the other end portion such that the second thread 64 at least partially encircles the target strut. For example, the second thread 64 may pass over three struts and loop around a fourth strut (i.e., the target strut) as shown in FIG. 5. The two end portions of the second thread 64 may be tied in a knot 65 which may be pulled tight as shown in FIG. 6 to form another half of the diameter reducing tie 60. This may cause the struts between the release wire 72 and the knot 65 to be pulled closer to one another. Excess portions of the second thread 64 extending beyond the knot 65 may be trimmed as shown in FIG. 6. Additional diameter reducing ties may be applied to other stents of the prosthesis 10 to retain the prosthesis in the reduced diameter configuration along a greater portion of the length thereof as described below.

Figure 7:
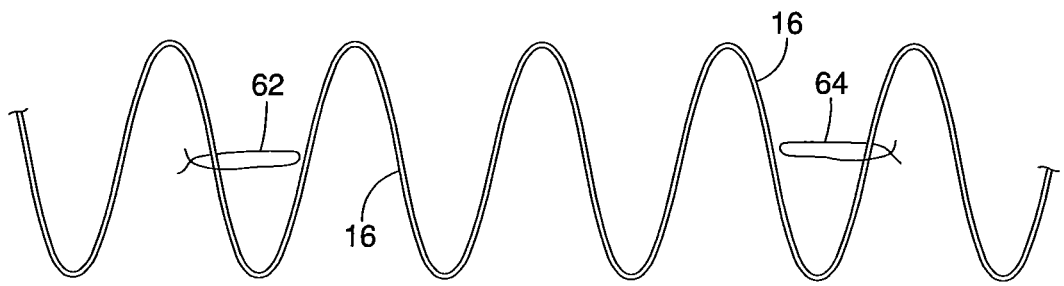
FIG. 7 depicts the diameter reducing tie of FIG. 5 after release of a release wire.

Removal of the release wire 72 from engagement with the threads 62, 64 may enable expansion of the stent 16 from the reduced diameter configuration to the expanded configuration as shown in FIG. 7. The release wire 72 may be removed by moving the release wire longitudinally relative to the graft material 14 and/or the stent 16. For example, the release wire 72 may be pulled distally with respect to the graft material 14 and the stent 16 a sufficient distance such that a proximal end of the release wire may become unthreaded from the graft material and may slide out of engagement with the threads 62, 64 of the diameter reducing tie. With the threads 62, 64 no longer engaged by the release wire 72, the stent 16 may expand to the expanded configuration. The knotted first and/or second threads 62, 64 may remain looped around the respective target struts as shown in FIG. 7. The diameter reducing tie also may be released by any other means including, for example, severing the thread 62 and/or the thread 64 or releasing the knot 63 and/or the knot 65.

One or more diameter reducing ties may be applied to one or more stents 16 of the prosthesis 10 to retain at least a portion of the prosthesis in the reduced diameter configuration. For example, the circumferential distance between the release wire 72 and each of the target struts in the reduced diameter configuration may be about 50 to about 75 percent less than the distance between the release wire and the corresponding target struts in the expanded configuration. In this example, if the distance in the expanded configuration is 15 mm, the distance in the reduced diameter configuration may be about 5 mm. Thus, in this example, the circumference of the stent 16 in the reduced diameter configuration may be about 20 mm less than the circumference of the stent in the expanded configuration (10 mm attributable to each thread 62, 64). If the diameter of the stent 16 in the expanded configuration is 36 mm, the diameter of the stent in the reduced diameter configuration may be about 30 mm. The diameter of the prosthesis 10 in the reduced diameter configuration may be less than the diameter of a portion of a body vessel into which the prosthesis is to be placed. Such a reduced diameter may enable the prosthesis 10 in the reduced diameter configuration to be repositioned or maneuvered within the body vessel for precise placement of the prosthesis prior to complete expansion of the prosthesis to the expanded configuration upon release of the diameter reducing ties as described above.

The diameter reducing tie 60 may include two threads, the threads extending in opposite directions relative to one another as described above. Alternatively, a diameter reducing tie may include only one thread extending in one direction transverse to the release wire. The threads may engage the stent 16 and/or the graft material 14 of the prosthesis 10. The diameter reducing tie also may have any other configuration suitable to retain the stent 16 in the reduced diameter configuration. In one example, the diameter reducing tie may be configured as one or more threads circumscribing a circumference of the stent 16 to retain the stent in the reduced diameter configuration. In another example, the graft material 14, as opposed to the threads, may be used to retain the stent 16 in the reduced diameter. For example, a release wire may be threaded through the graft material 14 at multiple circumferential locations along the stent 16. The wire may be pulled taught to gather the graft material 14 together and retain the stent 16 in the reduced diameter. Such alternative embodiments are within the scope of this disclosure.

Figure 8:
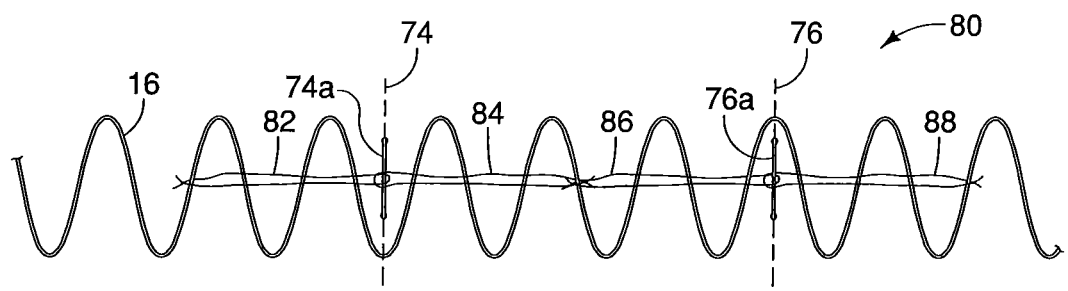
FIG. 8 depicts the formation of another example of a diameter reducing tie.
Figure 9:
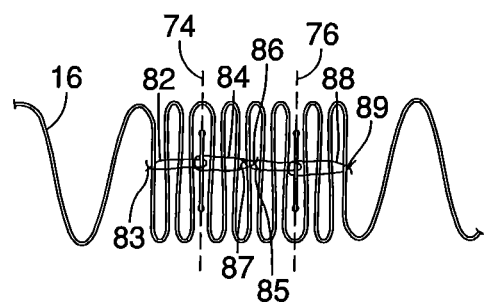
FIG. 9 depicts the diameter reducing tie formed as shown in FIG. 8.
Figure 10:
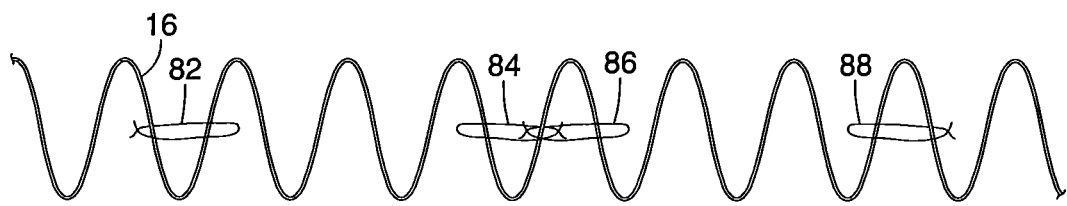
FIG. 10 depicts the diameter reducing tie of FIG. 9 after release of a release wire.

Diameter reducing ties may be applied to the prosthesis 10 at multiple locations to retain the prosthesis, or a portion thereof, in the reduced diameter configuration. For example, one or more diameter reducing ties may be applied to one or more stents along the length of the prosthesis 10. For example, a diameter reducing tie may be applied to each stent along the length of the prosthesis 10. In this manner, the prosthesis 10 may be retained in the reduced diameter configuration along substantially the entire length thereof. Each of the diameter reducing ties may be engaged by a common release wire such that each of the diameter reducing ties may be released by retraction of a single release wire. Alternatively, multiple release wires may be used such that different portions of the prosthesis 10 may be allowed to expand by selectively releasing one or more of the release wires.

Where a greater reduction in diameter is desired, a double diameter reducing tie may be applied to the prosthesis 10. FIGS. 8-10 depict the application of one example of a double diameter reducing tie 80 to the stent 16. Two release wires 74, 76 may be stitched along the graft material 14 of the prosthesis 10. The release wires 74, 76 may be substantially parallel to one another and spaced apart by multiple struts of the stent 16. The release wire 74 may be stitched longitudinally along the graft material 14, with a stitch 74a being positioned outside of the prosthesis (e.g., along the external surface 20 of the graft material 14) in the region of the stent 16. The release wire 76 may be stitched longitudinally along the graft material 14, with a stitch 76a being positioned outside of the prosthesis (e.g., along the external surface 20 of the graft material 14) in the region of the stent 16. A first thread 82 may be looped around the release wire 74 such that an intermediate portion of the first thread at least partially encircles the release wire and opposing end portions of the first thread extend in a first direction transverse to the release wire 74 and away from the release wire 76 as shown in FIG. 8. Each of the end portions of the first thread 82 may pass over one or more struts of the stent 16. One of the end portions then may pass over a target strut and the other end portion may pass under the target strut. One of the end portions may overlap the other end portion such that the first thread 82 at least partially encircles the target strut. For example, the first thread 82 may pass over three struts and loop around a fourth strut (i.e., a target strut) as shown in FIG. 8. The two end portions of the first thread 82 may be tied in a knot 83 and pulled tight as shown in FIG. 9 to form one part of the double diameter reducing tie. This may cause the struts between the release wire 74 and the knot 83 to be pulled closer to one another. Excess portions of the first thread 82 may be trimmed as shown in FIG. 9.

A second thread 84 may be applied in a similar manner to another portion of the stent 16. An intermediate portion of the second thread 84 may at least partially encircle the release wire 74 or the first thread 82. Opposing end portions of the second thread 84 may extend in a second direction transverse to the release wire 74 and toward the release wire 76 as shown in FIG. 8. Each of the end portions of the second thread 84 may pass over one or more struts of the stent 16. One of the end portions then may pass over a target strut and the other end portion may pass under the target strut. One of the end portions may overlap the other end portion such that the second thread 84 at least partially encircles the target strut. For example, the second thread 84 may pass over three struts and loop around a fourth strut (i.e., the target strut) as shown in FIG. 8. The two end portions of the second thread 84 may be tied in a knot 85 which may be pulled tight as shown in FIG. 9 to form another portion of the double diameter reducing tie 80. This may cause the struts between the release wire 72 and the knot 85 to be pulled closer to one another. Excess portions of the second thread 84 extending beyond the knot 85 may be trimmed as shown in FIG. 9.

A third thread 86 and a fourth thread 88 may be applied extending in opposite directions from the release wire 76 in a similar manner. Opposing end portions of the third thread 86 may be tied in a knot 87 to at least partially encircle the release wire 76 and a target strut as shown in FIG. 9. The third thread 86 may be looped around the same target strut as the second thread 84. In other words, the knots 85, 87 may be positioned on opposing sides of the same strut of the stent 16 as shown in FIG. 9. Opposing end portions of the fourth thread 88 may be tied in a knot 89 to at least partially encircle the release wire 76 or the third thread 86 and a target strut also as shown in FIG. 9.

The double diameter reducing tie may include two diameter reducing ties configured generally as shown in FIGS. 5-7 and applied to the same stent 16 as shown in FIGS. 8-10. By using double diameter reducing ties, the circumference of the stent 16 in the reduced diameter configuration may be less than (e.g., half) the diameter of the stent in the reduced diameter configuration as described above with reference to FIGS. 5-7. For example, the circumference of the stent 16 in the reduced diameter configuration may be about 40 mm less than the circumference of the stent in the expanded configuration, as opposed to 20 mm less as described above. Thus, a prosthesis having a diameter of 36 mm in the expanded configuration may have a diameter of about 23 mm in the reduced diameter configuration. This temporary restraint of the prosthesis 10 in the reduced diameter configuration may enable movement or repositioning of the prosthesis 10 within the body vessel even after deployment from a delivery device. In other words, even after the sheath is removed and the prosthesis 10 is allowed to expand from the delivery configuration to the reduced diameter configuration, the diameter of the prosthesis may be less than the diameter of the body vessel in which the prosthesis is placed. Thus, the prosthesis 10 may be repositioned prior to release of the diameter reducing ties and complete expansion of the prosthesis to the expanded configuration.

FIGS. 11-14 illustrate a series of diameter reducing ties applied to the prosthesis 10 in one known configuration. FIGS. 11-12 are perspective views of the anterior side and the posterior side, respectively, of the prosthesis 10. Diameter reducing ties may be applied to the posterior side of the prosthesis 10 as further described below. In this example, the diameter reducing ties are configured as a series of double diameter reducing ties as described above with reference to FIGS. 8-10. A first release wire 174 may extend longitudinally along the graft material 14 of the prosthesis 10. The first release wire 174 may be stitched in and out of the graft material 14 such that external stitches 174a may be positioned external to the prosthesis 10 in regions corresponding to the stents 16. For example, an external stitch 174a may correspond to each stent 16 along the length of the prosthesis as shown in FIG. 12. A second release wire 176 also may extend longitudinally along the graft material 14 of the prosthesis 10. The second release wire 176 may be stitched in and out of the graft material 14 such that external stitches 176a may be positioned external to the prosthesis 10 in regions corresponding to the stents 16. For example, an external stitch 176a may correspond to each stent 16 along the length of the prosthesis 10. The first and second release wires 174, 176 may be generally parallel to one another and may be positioned at substantially equal distances from the posterior point of the prosthesis 10. The posterior point of the prosthesis 10 may extend generally longitudinally along the body of the prosthesis and may be substantially circumferentially centered on the posterior side of the prosthesis. The posterior point of the prosthesis 10 may be positioned on the graft body 14 approximately 180 degrees from the anterior point of the prosthesis with respect to the circumference of the prosthesis. A series of threads may be looped around the release wires 174, 176 and target struts of each of the stents 16 as described above with reference to FIGS. 8-10. In this manner, each stent 16 of the prosthesis 10 may be retained in the reduced diameter configuration by a diameter reducing tie.

The series of double diameter reducing ties may be arranged in a substantially linear pattern extending generally longitudinally along the prosthesis 10. The series of diameter reducing ties may be positioned generally symmetrically with respect to the posterior point of the prosthesis 10 such that the release wires 174, 176 may be positioned on opposite sides of the posterior point and approximately equal distances from the posterior point. In other words, the series of double diameter reducing ties may be positioned generally opposite the anterior point of the prosthesis (and thus opposite the fenestration 38 and the scallop 40) with respect to the circumference of the prosthesis. The series of diameter reducing ties may extend along substantially an entire length of the prosthesis 10. For example, a distal-most diameter reducing tie of the series of diameter reducing ties may be positioned proximate the distal end 24 of the prosthesis 10, and a proximal-most diameter reducing tie of the series of diameter reducing ties may be positioned proximate the proximal end 22 of the prosthesis. In this manner, the prosthesis 10 may be retained in the reduced diameter configuration along substantially the entire length thereof.

Figure 13:
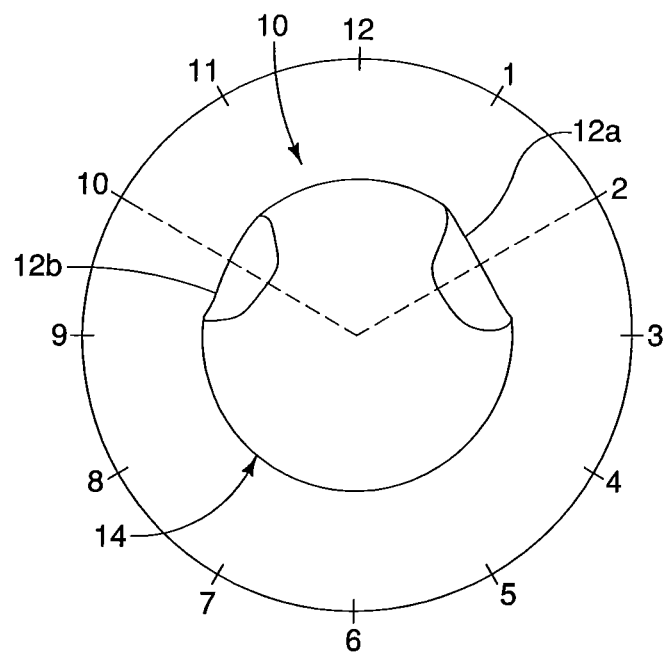
FIG. 13 is a cross sectional view taken along line A-A in FIGS. 11-12 with the prosthesis in an expanded configuration.
Figure 14:
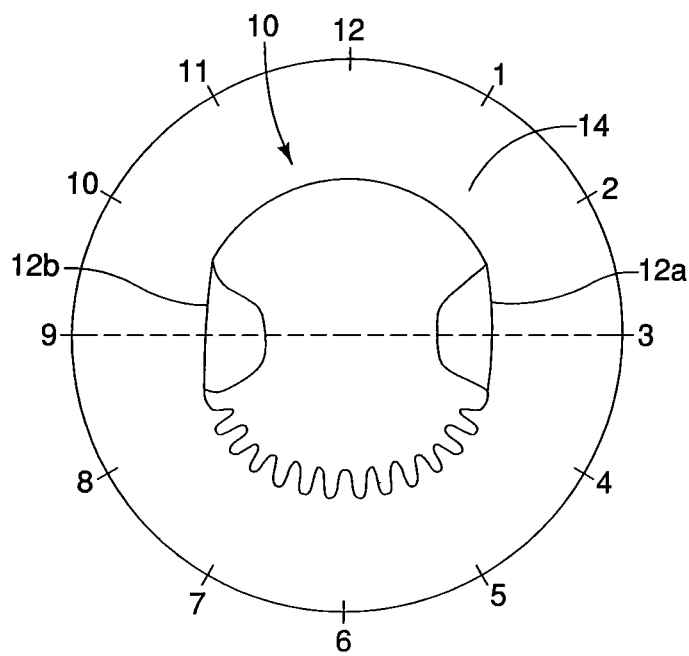
FIG. 14 is a cross sectional view taken along line A-A in FIGS. 11-12 with the prosthesis in a reduced diameter configuration.

FIG. 13 is a transverse cross sectional view taken along line A-A in FIG. 11 with the prosthesis 10 in the expanded configuration. The circumferential positions of various components or features of the prosthesis 10 may be described with reference to a clock face as shown in FIGS. 13-14. For example, the clock face may be positioned such that 12 o'clock corresponds to the anterior point of the prosthesis 10 and 6 o'clock corresponds to the posterior point of the prosthesis. Thus, the fenestration 38 and/or the scallop 40 may be positioned at approximately 12 o'clock (i.e., along the anterior point of the prosthesis 10). In the expanded configuration, the pivotable fenestrations 12a, 12b may be positioned circumferentially on the prosthesis 10 at approximately 2 o'clock and 10 o'clock, respectively, as shown in FIG. 13. Such positioning may enable the pivotable fenestrations 12a, 12b to generally align with the renal arteries as described above when the prosthesis 10 is allowed to expand to the expanded configuration within the aorta of a patient.

FIG. 14 is a transverse cross sectional view taken along line A-A in FIG. 11 with the prosthesis 10 in the reduced diameter configuration having diameter reducing ties applied as shown in FIGS. 11-12. Because the double diameter reducing ties may be applied to the posterior side of the prosthesis 10 (i.e., with the release wires 174, 176 positioned on opposite sides of approximately 6 o'clock), the reduced circumference of the prosthesis may be achieved by restraining a portion of the posterior side of the prosthesis (i.e., by preventing expansion of a portion of the posterior side of the prosthesis to the expanded configuration). This may result in the graft material 14 being bunched or gathered along the posterior side of the prosthesis 10 as shown in FIG. 14. The circumferential length of the posterior side of the prosthesis 10 in the reduced diameter configuration may be less than the circumferential length of the posterior side of the prosthesis in the expanded configuration. Because the anterior side of the prosthesis 10 may be substantially unrestrained by the diameter reducing ties, the circumferential length of the anterior side of the prosthesis in the reduced diameter configuration may be substantially the same as the circumferential length of the anterior side of the prosthesis in the expanded configuration. Thus, the angular positions of the pivotable fenestrations 12a, 12b with respect to one another may change as the prosthesis 10 is allowed to expand from the reduced diameter configuration to the expanded configuration. In other words, the pivotable fenestrations 12 may be pulled circumferentially toward the posterior point of the prosthesis 10 by the gathering of the graft material 14 along the posterior side of the prosthesis in the reduced diameter configuration. For example, in the reduced diameter configuration, the pivotable fenestrations 12a, 12b may be positioned circumferentially on the prosthesis 10 at approximately 3 o'clock and 9 o'clock, respectively as shown in FIG. 14. As the prosthesis 10 is allowed to expand to the expanded configuration, the pivotable fenestrations 12a, 12b may be allowed to move toward approximately 2 o'clock and 10 o'clock as shown in FIG. 13. Such a change in the angular positions of the pivotable fenestrations 12 upon expansion of the prosthesis into the expanded configuration may cause difficulty in positioning the prosthesis properly during deployment and/or cannulation of the branch vessels while the diameter reducing ties are in place. In other words, the pivotable fenestrations may not properly align with branching vessels as intended when the prosthesis is in either the reduced diameter configuration or the expanded configuration.

Figure 15:
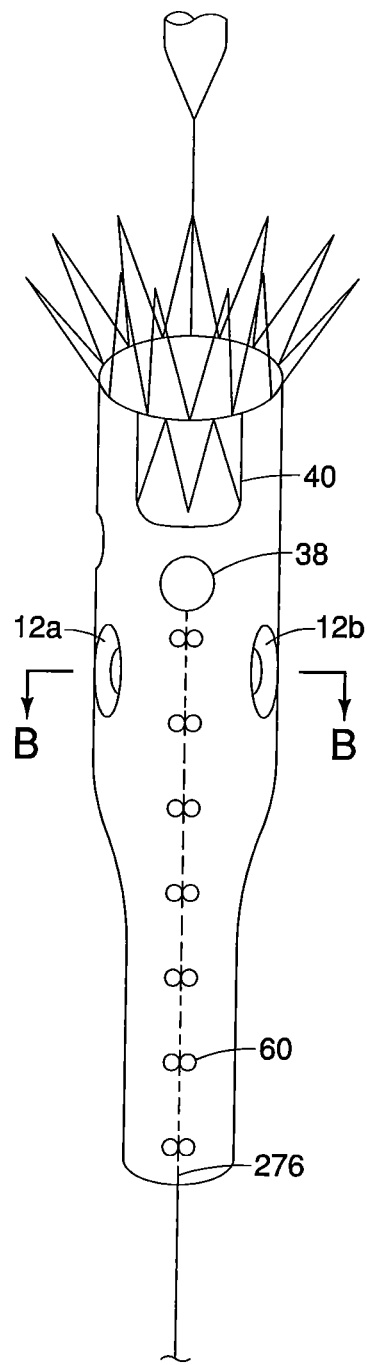
FIG. 15 is a perspective view of an anterior side of the prosthesis of FIG. 1 having diameter reducing ties applied thereto in another exemplary configuration.
Figure 16:
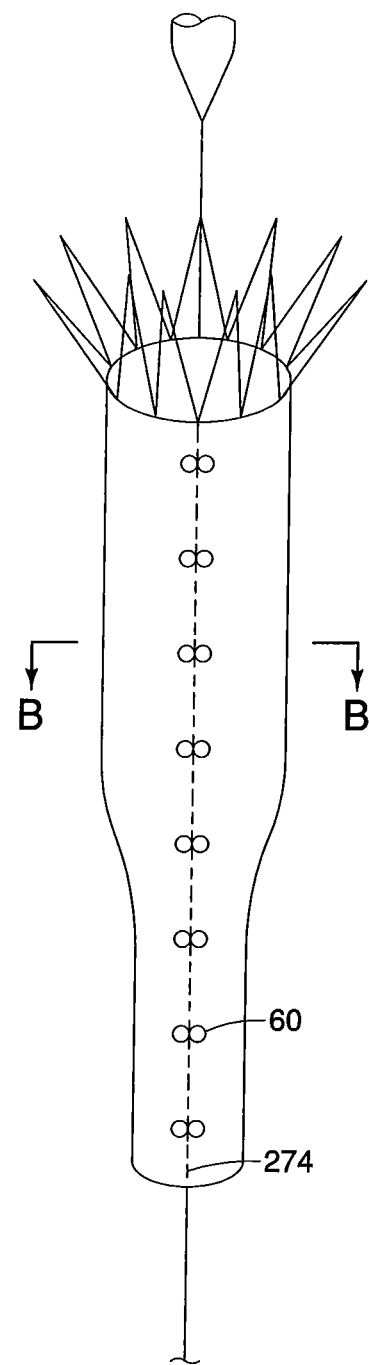
FIG. 16 is a perspective view of a posterior side of the prosthesis of FIG. 15.
Figure 17:
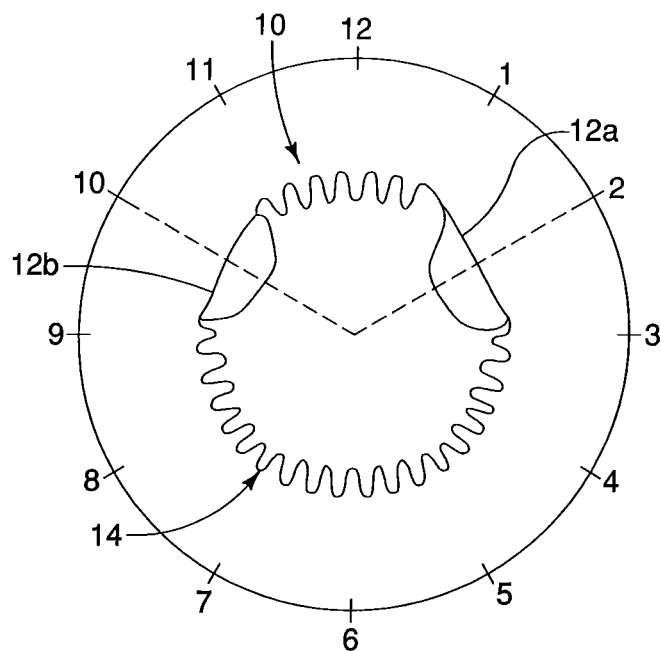
FIG. 17 is a cross sectional view taken along line B-B in FIGS. 15-16 with the prosthesis in a reduced diameter configuration.

It may be desirable to avoid a change in the angular positions of the fenestrations 12 upon expansion of the prosthesis 10 from the reduced diameter configuration to the expanded configuration as described above. To that end, FIGS. 15-17 illustrate a series of diameter reducing ties applied to the prosthesis 10 in one exemplary configuration. FIGS. 15 and 16 are views of the anterior side and the posterior side, respectively, of the prosthesis 10. Diameter reducing ties may be applied to the anterior and posterior sides of the prosthesis 10 as further described below. In this example, the diameter reducing ties are configured as two series of diameter reducing ties, each diameter reducing tie being configured as described above with reference to FIGS. 5-7. The first series of diameter reducing ties may be applied to the posterior side of the prosthesis as shown in FIG. 16. For example, a first release wire 274 may extend longitudinally along the graft material 14 of the prosthesis 10. The first release wire 274 may be positioned circumferentially on the posterior point of the prosthesis and may be stitched in and out of the graft material 14 as described above with reference to the release wire 174. A series of threads may be looped around the release wire 274 and target struts of the stents 16 to form the diameter reducing ties. In this manner, a posterior portion of each stent 16 of the prosthesis 10 may be restrained in the reduced diameter configuration. The first series of diameter reducing ties may be arranged in a substantially linear pattern extending generally longitudinally along the posterior point of the prosthesis 10. The first series of diameter reducing ties may extend along substantially an entire length of the prosthesis 10 to restrain each of the stents 16 of the prosthesis along substantially the entire length of the prosthesis.

Similarly, the second series of diameter reducing ties may be applied to the anterior side of the prosthesis as shown in FIG. 15. For example, a second release wire 276 may extend longitudinally along the graft material 14 of the prosthesis 10. The second release wire 276 may be positioned circumferentially on the anterior point of the prosthesis 10 and may be stitched in and out of the graft material 14 as described above with reference to the release wire 176. A series of threads may be looped around the release wire 276 and target struts of the stents 16 to form the diameter reducing ties. The second series of diameter reducing ties may be arranged in a substantially linear pattern extending generally longitudinally along the anterior point of the prosthesis 10. The second series of diameter reducing ties may extend along a portion of the length of the prosthesis 10 extending from a point proximate the distal end 24 of the prosthesis to an intermediate point proximate and distal to the fenestration 38, as shown in FIG. 15, to restrain each of the stents of the prosthesis along a portion of the length of the prosthesis distal to the fenestration 38.

In the expanded configuration, the pivotable fenestrations 12a, 12b may be positioned circumferentially on the prosthesis 10 at approximately 2 o'clock and 10 o'clock, respectively, as shown in FIG. 13. FIG. 17 is a transverse cross sectional view taken along line B-B in FIG. 15 with the prosthesis 10 in the reduced diameter configuration. Because the diameter reducing ties may be applied to both the anterior and posterior sides of the prosthesis 10 (i.e., at approximately 12 o'clock and 6 o'clock), the circumferential lengths of both the anterior and posterior sides of the prosthesis may be restrained by the diameter reducing ties. In other words, the circumferential length of the posterior side of the prosthesis 10 in the reduced diameter configuration may be less than the circumferential length of the posterior side of the prosthesis in the expanded configuration. The circumferential length of the anterior side of the prosthesis 10 in the reduced diameter configuration also may be less than the circumferential length of the anterior side of the prosthesis in the expanded configuration. This may result in the graft material 14 being bunched or gathered along both the anterior and posterior sides of the prosthesis 10 as shown in FIG. 17. With both the anterior and posterior sides of the prosthesis 10 restrained by diameter reducing ties, the pivotable fenestrations 12a, 12b may be positioned at approximately 2 o'clock and 10 o'clock, respectively with the prosthesis in the reduced diameter configuration. Restraining both the anterior and posterior sides of the prosthesis 10 with diameter reducing ties, as opposed to restraining only one side of the prosthesis, may help to reduce any change in the angular positions of the pivotable fenestrations 12a, 12b with respect to one another upon expansion of the prosthesis to the expanded configuration. In other words, unlike prostheses restrained using conventional diameter reducing tie arrangements, the pivotable fenestrations 12a, 12b may have substantially the same circumferential positions on the prosthesis 10 (e.g., approximately 2 o'clock and 10 o'clock, respectively) regardless of whether the prosthesis is in the reduced diameter configuration, as shown in FIG. 17, or the expanded configuration, as shown in FIG. 13.

Positioning diameter reducing ties on both the anterior side and the posterior side of the prosthesis 10 may enable a physician to use the diameter reducing ties to adjust the relative positions of the pivotable fenestrations 12 during deployment of the prosthesis. For example, the physician may release the first series of diameter reducing ties from the posterior side of the prosthesis 10 and the second series of diameter reducing ties from the anterior side of the prosthesis approximately simultaneously. Thus, the relative circumferential positions of the pivotable fenestrations 12a, 12b may remain substantially constant during expansion of the prosthesis 10 from the reduced diameter configuration to the expanded configuration.

Alternatively, the physician may release the first and second series of diameter reducing ties sequentially by, for example, pulling the respective release wires sequentially, to manipulate the relative circumferential positions of the pivotable fenestrations 12a, 12b. For example, the physician may release the first series of diameter reducing ties from the posterior side of the prosthesis 10 before releasing the second series of diameter reducing ties from the anterior side of the prosthesis. The anterior side of the prosthesis 10 may remain compressed after expansion of the posterior side of the prosthesis. Thus, the angular positions of the pivotable fenestrations 12a, 12b may change upon release of the first series of diameter reducing ties. For example, the pivotable fenestrations 12a, 12b may move angularly toward the 12 o'clock position. Alternatively, the physician may release the second series of diameter reducing ties from the anterior side of the prosthesis 10 before releasing the first series of diameter reducing ties from the posterior side of the prosthesis. The posterior side of the prosthesis 10 may remain compressed after expansion of the anterior side of the prosthesis. Thus, the angular positions of the pivotable fenestrations 12a, 12b may change upon release of the second series of diameter reducing ties. For example, the pivotable fenestrations 12a, 12b may move toward the 6 o'clock position. In this manner, the physician may manipulate the relative circumferential positions of the pivotable fenestrations 12a, 12b as desired for proper alignment with branch vessels during deployment of the prosthesis 10.

When the diameter reducing ties are applied to the prosthesis 10 as shown in FIGS. 15-17, it may be desirable to restrain a portion of the anterior side of the prosthesis longitudinally proximal to the fenestration 38. This may allow the prosthesis 10 to be restrained in the reduced diameter configuration along substantially the entire length thereof as described above. To that end, the second series of diameter reducing ties may further extend proximally along the anterior side of the prosthesis 10. However, it may also be desirable to avoid positioning threads and/or release wires of diameter reducing ties over the openings of the prosthesis 10 such as, for example, the fenestration 38 and/or the scallop 40.

Figure 18:
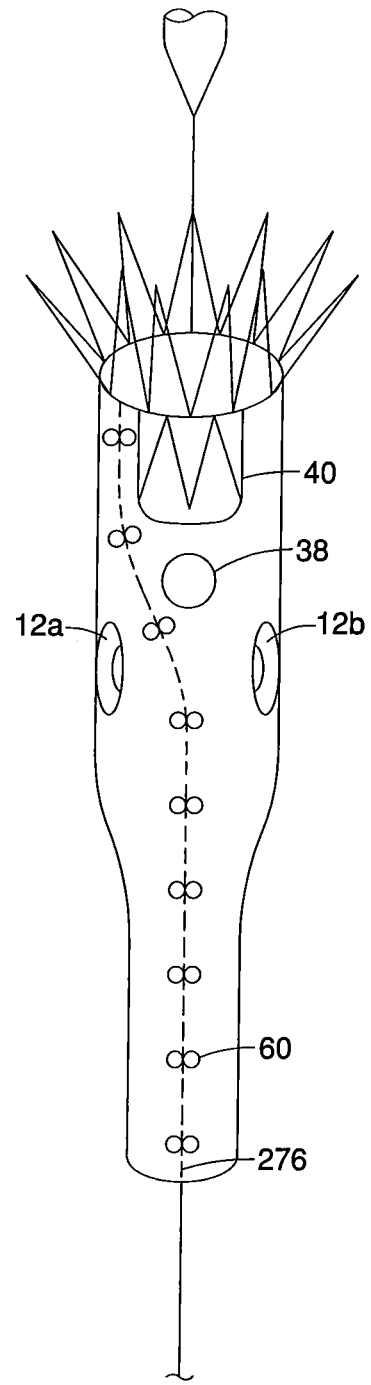
FIG. 18 is a perspective view of an anterior side of the prosthesis of FIG. 1 having diameter reducing ties applied thereto in another exemplary configuration.

In one example, shown in FIG. 18, the second series of diameter reducing ties may extend generally longitudinally and partly circumferentially along the anterior side of the prosthesis. A first portion of the second series of diameter reducing ties may be positioned longitudinally distal to the fenestration 38. A second portion of the second series of diameter reducing ties may be positioned longitudinally adjacent or proximal to the fenestration 38. Each diameter reducing tie of the second portion of the second series of diameter reducing ties (e.g., the diameter reducing ties positioned proximal to the fenestration 38) may be offset circumferentially from the anterior point of the prosthesis 10. In other words, the diameter reducing ties positioned longitudinally proximal to the fenestration 38 may be positioned circumferentially to one side of, or adjacent to, the fenestration 38 and/or the scallop 40. The diameter reducing ties may be offset sufficiently from the anterior point of the prosthesis 10 so as not to overlap the fenestration 38 or the scallop 40.

The second release wire 276 may extend generally longitudinally and circumferentially along the prosthesis 10 to engage each of the diameter reducing ties of the second series of diameter reducing ties. The second series of diameter reducing ties may be offset circumferentially to either side of the anterior point of the prosthesis. For example, the release wire 276 may pass between the fenestration 38 and the pivotable fenestration 12a as shown in FIG. 18. Alternatively, the release wire 276 may pass between the fenestration 38 and the pivotable fenestration 12b. Providing diameter reducing ties in this arrangement may enable the stents positioned proximal to the fenestration 30 to be further restrained by the second series of diameter reducing ties, whereby the prosthesis may be restrained in the reduced diameter configuration along substantially the entire length thereof.

Figure 19:
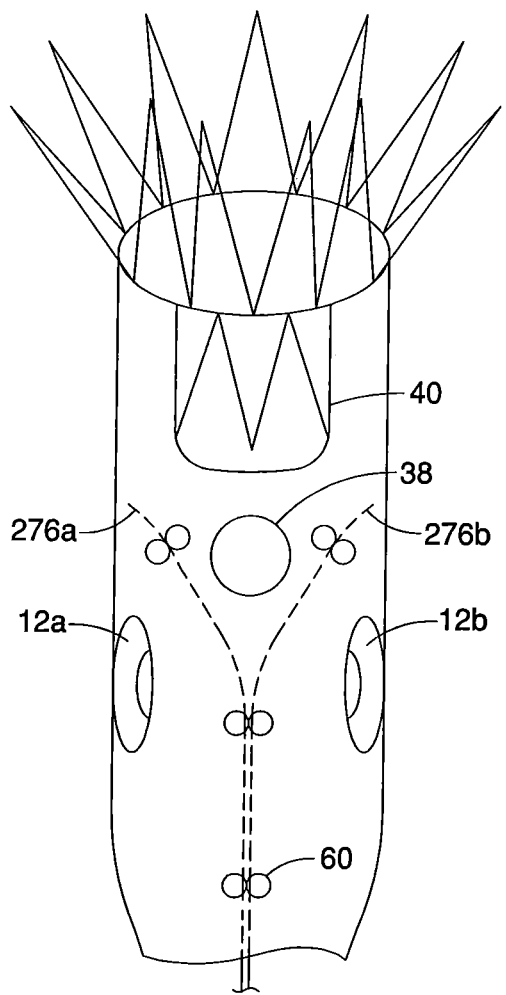
FIG. 19 is a partial perspective view of an anterior side of the prosthesis of FIG. 1 having diameter reducing ties applied thereto in another exemplary configuration.

In another example, shown in FIG. 19, the second portion of the second series of diameter reducing ties may include one or more diameter reducing ties positioned circumferentially on opposing sides of the fenestration 38. A release wire 276a may extend generally longitudinally along the anterior point of the prosthesis 10 to engage one or more of the diameter reducing ties of the first portion of the second series of diameter reducing ties (e.g., the diameter reducing ties positioned distal to the fenestration 38). The release wire 276a then may extend generally longitudinally and circumferentially from a diameter reducing tie proximate and distal to the fenestration 38 (e.g., proximate the intermediate point) between the fenestration 38 and the pivotable fenestration 12a to engage one or more diameter reducing ties of the second portion of the second series of diameter reducing ties (e.g., the diameter reducing ties positioned proximal to the fenestration 38). Similarly, a release wire 276b may extend generally longitudinally along the anterior point of the prosthesis 10 to engage one or more of the diameter reducing ties of the first portion of the second series of diameter reducing ties (e.g., the diameter reducing ties positioned distal to the fenestration 38). The release wire 276b then may extend generally longitudinally and circumferentially from a diameter reducing tie proximate and distal to the fenestration 38 (e.g., proximate the intermediate point) between the fenestration 38 and the pivotable fenestration 12b to engage one or more diameter reducing ties of the second portion of the second series of diameter reducing ties (e.g., the diameter reducing ties positioned proximal to the fenestration 38). The release wires 276a, 276b may cooperatively form a Y shape, as shown in FIG. 19, with the leg of the Y positioned generally along the anterior point of the prosthesis 10 and the arms of the Y extending longitudinally and circumferentially on opposing sides of the fenestration 38.

In an alternative embodiment, the release wire 276b may engage only the diameter reducing ties positioned proximal to the fenestration 38 and circumferentially on the opposite side of the fenestration 38 from the release wire 276a. In this embodiment, the diameter reducing ties positioned distal to the fenestration 38 may be engaged by a single release wire (e.g., the release wire 276a) as opposed to multiple release wires (e.g., the release wires 276a, 276b).

Providing diameter reducing ties in this configuration may enable the prosthesis 10 to be restrained in the reduced diameter configuration along substantially the entire length thereof as described above. Providing diameter reducing ties in this configuration also may minimize any change in the angular positions of the pivotable fenestrations 12a, 12b relative to the fenestration 38 and/or the scallop 40 upon expansion of the prosthesis from the reduced diameter configuration to the expanded configuration. Because the stents 16 positioned proximal to the fenestration 38 may be restrained on both sides of the fenestration 38, the fenestration 38 may remain at approximately 12 o'clock while the pivotable fenestrations 12a, 12b may remain at approximately 2 o'clock and 10 o'clock, respectively, upon expansion of the prosthesis 10 from the reduced diameter configuration to the expanded configuration. Upon expansion of the prosthesis 10 from the reduced diameter configuration to the expanded configuration, circumferential portions of the stents 16 on opposing sides of the fenestration 38 may expand by substantially equal amounts so that the fenestration 30 may remain at approximately 12 o'clock during expansion of the prosthesis.

Figure 20:
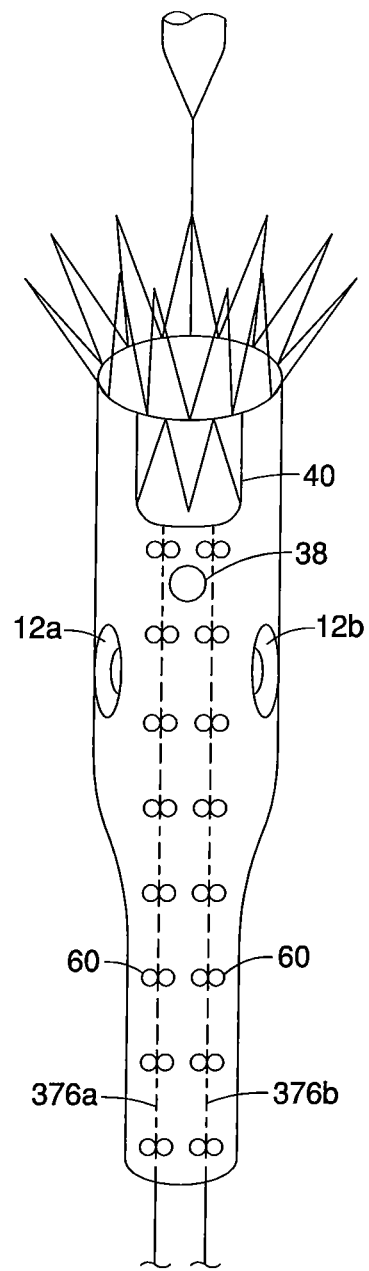
FIG. 20 is a perspective view of an anterior side of the prosthesis of FIG. 1 having diameter reducing ties applied thereto in another exemplary configuration.

FIG. 20 illustrates diameter reducing ties applied to the prosthesis 10 in yet another exemplary configuration. In this example, the diameter reducing ties are configured as four series of diameter reducing ties, each as described above with reference to FIGS. 5-7. The first and second series of diameter reducing ties may be applied to the posterior side of the prosthesis as described above with reference to FIG. 12. Alternatively, the first and second series of diameter reducing ties may be configured as a series of double diameter reducing ties as described above with reference to FIGS. 8-10. The third and fourth series of diameter reducing ties may be applied to the anterior side of the prosthesis 10. For example, a third release wire 376a may extend longitudinally along the graft material 14 of the prosthesis 10. The third release wire 376a may be positioned circumferentially between the anterior point of the prosthesis 10 and the pivotable fenestration 12a as shown in FIG. 20. The third release wire 376a may be stitched in and out of the graft material 14 as described above with reference to the release wire 176. A series of threads may be looped around the release wire 376a and target struts of the stents 16 to form the diameter reducing ties. The third series of diameter reducing ties may be arranged in a substantially linear pattern extending generally longitudinally along the prosthesis 10. The third series of diameter reducing ties may extend along a portion of the length of the prosthesis 10 extending from a point proximate the distal end 24 of the prosthesis to a point proximate and distal to the scallop 40, as shown in FIG. 20, to restrain each of the stents 16 of the prosthesis along a portion of the length thereof distal to the scallop 40. A fourth release wire 376b may engaged each of the diameter reducing ties of the fourth series of diameter reducing ties. The fourth series of diameter reducing ties may be substantially identical to the third series of diameter reducing ties and may be positioned circumferentially between the anterior point of the prosthesis 10 and the pivotable fenestration 12b also as shown in FIG. 20.

Providing diameter reducing ties in this configuration may enable the prosthesis 10 to be restrained in the reduced diameter configuration along substantially the entire length thereof as described above. Providing diameter reducing ties in this configuration also may minimize any change in the angular positions of the pivotable fenestrations 12a, 12b relative to the fenestration 38 and/or the scallop 40 upon expansion of the prosthesis 10 from the reduced diameter configuration to the expanded configuration also as described above. Such a four-series diameter reducing tie configuration may have the added benefit of restraining the prosthesis 10 in a reduced diameter configuration having a smaller diameter than may be achieved using a two-series diameter reducing tie configuration. The smaller diameter may be enabled by the additional two series of diameter reducing ties, one applied to the posterior side of the prosthesis and the other applied to the anterior side of the prosthesis.

In any of the examples described above, double diameter reducing ties may be used in place of single diameter reducing ties or vice versa. Features of one example may be combined with features of another example while remaining within the scope of this disclosure.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. An endoluminal prosthesis comprising:
    a tubular body of a biocompatible graft material having a proximal end, a distal end, an anterior side, and a posterior side,
    at least a first fenestration and a second fenestration in the graft material, the first and second fenestrations being spaced from one another circumferentially around the tubular body,
    at least one first diameter reducing tie positioned circumferentially on the posterior side of the prosthesis and directly between the first and second fenestrations and engaging at least a circumferential segment of the posterior side of the tubular body, the engaged segment of the posterior side being restrained from expansion by the first diameter reducing tie, and
    at least one second diameter reducing tie positioned circumferentially and directly between the first and second fenestrations on the anterior side of the prosthesis opposite the at least one first diameter reducing tie and engaging at least a circumferential segment of the anterior side of the tubular body, the engaged segment of the anterior side being restrained from expansion by the second diameter reducing tie,
    wherein at least a portion of the prosthesis is movable between a reduced diameter configuration and an expanded configuration, and circumferential angular position of the first fenestration in the expanded configuration is substantially the same as the circumferential angular position of the first fenestration in the reduced diameter configuration, and a circumferential angular position of the second fenestration in the expanded configuration is the same as the circumferential angular position of the second fenestration in the reduced diameter configuration.

2. The endoluminal prosthesis of claim 1, wherein the at least one second diameter reducing tie comprises a series of diameter reducing ties arranged in a substantially linear arrangement extending longitudinally along at least a portion of the length of the prosthesis.

3. The endoluminal prosthesis of claim 2, wherein a longitudinal position of the first fenestration is substantially the same as a longitudinal position of the second fenestration and the series of diameter reducing ties extends longitudinally between the distal end of the prosthesis and the longitudinal positions of the first and second fenestrations.

4. The endoluminal prosthesis of claim 1, wherein the at least one first diameter reducing tie comprises a first series of diameter reducing ties arranged in a substantially linear arrangement extending longitudinally along at least a portion of the length of the prosthesis, and the at least one second diameter reducing tie comprises a second series of diameter reducing ties arranged in a substantially linear arrangement extending longitudinally along at least a portion of the length of the prosthesis.

5. The endoluminal prosthesis of claim 4, further comprising a third fenestration positioned circumferentially on an anterior point of the prosthesis and longitudinally proximal of the first and second fenestrations.

6. The endoluminal prosthesis of claim 5, further comprising at least one proximal diameter reducing tie positioned circumferentially on the anterior side of the prosthesis and misaligned with the third fenestration and longitudinally proximal of the second series of diameter reducing ties.

7. The endoluminal prosthesis of claim 6, wherein a release wire extends generally longitudinally and partly circumferentially along the prosthesis and engages each of the diameter reducing ties of the second series of diameter reducing ties and the at least one proximal diameter reducing tie.

8. The endoluminal prosthesis of claim 6, wherein the at least one proximal diameter reducing tie comprises at least one first proximal diameter reducing tie positioned circumferentially misaligned with the third fenestration in a first circumferential direction and at least one second proximal diameter reducing tie positioned circumferentially misaligned with the third fenestration in a second circumferential direction generally opposite the first circumferential direction.

9. The endoluminal prosthesis of claim 8, wherein a release wire engages the at least one first proximal diameter reducing tie and another release wire engages the at least one second proximal diameter reducing tie.

10. The endoluminal prosthesis of claim 1, wherein at least one of the first and second fenestrations comprises a pivotable fenestration.

11. The endoluminal prosthesis of claim 1, wherein an engaged length of the circumferential segment of the posterior side and an engaged length of the circumferential segment of the anterior side are dimensioned relative to one another such that, upon movement of the prosthesis between the reduced diameter configuration and the expanded configuration, the angular positions of the first fenestration and the second fenestration relative to one another are unchanged.

12. An endoluminal prosthesis comprising:
a tubular body of a biocompatible graft material having a proximal end, a distal end, and at least one stent positioned on the graft material;
a first series of diameter reducing ties positioned circumferentially on a posterior side of the prosthesis and arranged in a substantially linear arrangement extending generally longitudinally between the proximal and distal ends of the prosthesis, each diameter reducing tie of the first series of diameter reducing ties engaged by a first release wire and engaging a circumferential segment of the posterior side of the prosthesis to restrain the engaged segment from expansion, wherein the first series of diameter reducing ties extends along substantially an entire length of the prosthesis; and
a second series of diameter reducing ties positioned circumferentially on an anterior side of the prosthesis and engaged by a second release wire, each diameter reducing tie of the second series of diameter reducing ties engaging a circumferential segment of the anterior side of the prosthesis to restrain the engaged segment from expansion, the second series of diameter reducing ties comprising a substantially linear arrangement extending longitudinally from the distal end of the prosthesis to an intermediate point along a length of the prosthesis, and for a length less than the length of the prosthesis, and
a set of fenestrations on the anterior side of the prosthesis, wherein at least a portion of the prosthesis is movable between a reduced diameter configuration and an expanded configuration, and wherein the relative circumferential angular orientation of the fenestrations is the same in the reduced diameter configuration and the expanded configuration.

13. The endoluminal prosthesis of claim 12, further comprising a third series of diameter reducing ties positioned longitudinally proximal of the second series of diameter reducing ties and circumferentially on the anterior side of the prosthesis and offset from the second series of diameter reducing ties.

14. The endoluminal prosthesis of claim 13, wherein each diameter reducing tie of the third series of diameter reducing ties is engaged by the second release wire.

15. The endoluminal prosthesis of claim 13, further comprising a fourth series of diameter reducing ties positioned longitudinally proximal of the second series of diameter reducing ties and circumferentially on the anterior side of the prosthesis and offset from the second series of diameter reducing ties, wherein the third series of diameter reducing ties is offset from the second series of diameter reducing ties in a first circumferential direction, and the fourth series of diameter reducing ties is offset from the second series of diameter reducing ties in a second circumferential direction generally opposite the first circumferential direction.

16. The endoluminal prosthesis of claim 15, wherein the second series of diameter reducing ties, the third series of diameter reducing ties, and the fourth series of diameter reducing ties collectively comprise a substantially Y shaped arrangement extending longitudinally and partly circumferentially between the proximal and distal ends of the prosthesis.

17. The endoluminal prosthesis of claim 15, wherein each diameter reducing tie of the third series of diameter reducing ties is engaged by the second release wire and each diameter reducing tie of the fourth series of diameter reducing ties is engaged by a third release wire.

* * * * *